(12) United States Patent
Montminy

(10) Patent No.: US 9,693,994 B2
(45) Date of Patent: Jul. 4, 2017

(54) CLASS IIA HDAC INHIBITORS FOR THE TREATMENT OF INFECTION

(71) Applicant: Research Development Foundation, Carson City, NV (US)

(72) Inventor: Marc Montminy, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 64 days.

(21) Appl. No.: 14/682,263

(22) Filed: Apr. 9, 2015

(65) Prior Publication Data
US 2015/0290168 A1 Oct. 15, 2015

Related U.S. Application Data

(60) Provisional application No. 61/977,481, filed on Apr. 9, 2014.

(51) Int. Cl.
| | | |
|---|---|---|
| *A61K 31/19* | (2006.01) | |
| *A61K 31/40* | (2006.01) | |
| *A61K 45/06* | (2006.01) | |
| *A61K 39/40* | (2006.01) | |
| *A61K 31/137* | (2006.01) | |
| *A61K 31/165* | (2006.01) | |
| *A61K 31/166* | (2006.01) | |
| *A61K 31/20* | (2006.01) | |

(52) U.S. Cl.
CPC ............ *A61K 31/40* (2013.01); *A61K 31/137* (2013.01); *A61K 31/165* (2013.01); *A61K 31/166* (2013.01); *A61K 31/19* (2013.01); *A61K 31/20* (2013.01); *A61K 39/40* (2013.01); *A61K 45/06* (2013.01)

(58) Field of Classification Search
CPC .. A61K 31/137; A61K 31/165; A61K 31/166; A61K 39/40; A61K 31/40; A61K 39/01; A61K 45/06; A61K 31/20
See application file for complete search history.

(56) References Cited

U.S. PATENT DOCUMENTS 8,946,295 B2 * 2/2015 Chung .................. A61K 31/19
514/459

FOREIGN PATENT DOCUMENTS

| EP | 1 719 508 | 11/2006 |
|---|---|---|
| WO | WO 03/083067 | 10/2003 |
| WO | WO 2007/131364 | 11/2007 |
| WO | WO 2009/067543 | 5/2009 |
| WO | WO 2012011917 | * 1/2012 |

OTHER PUBLICATIONS

Baas, 2013 SciBX 6(13); 1-2 pages (Published online Apr. 4, 2013).*

Abu-Farha et al., "Proteomics Analysis of Human Obesity Reveals the Epigenetic Factor HDAC4 as a Potential Target for Obesity," *PLoS ONE*, 8:e75342, 2013.
Agarwal et al., "Cyclic AMP intoxication of macrophages by a *Mycobacterium tuberculosis* adenylate cyclase," *Nature*, 460:98-102, 2009.
Altarejos et al., "The Creb1 coactivator Crtc1 is required for energy balance and fertility," *Nat Med*, 14(10):1112-1117, 2008.
Appukuttan et al., "The related transcriptional enhancer factor-1 isoform, TEAD4$_{216}$, can repress vascular endothelial growth factor expression in mammalian cells," *PLoS ONE*, 7(6):e31260, 2012.
Arkan et al., "IKK-beta links inflammation to obesity-induced insulin resistance," *Nat Med*, 11:191-198, 2005.
Aronoff et al., "Cutting edge: macrophage inhibition by cyclic AMP (cAMP): differential roles of protein kinase A and exchange protein directly activated by cAMP-1," *J Immunol*, 174:595-599, 2005.
Baas, "Closer to class IIa HDAC inhibitors," *Science-Business Exchange*, 6(13):1-2, 2013.
Bardeesy et al., "Loss of the Lkb1 tumour suppressor provokes intestinal polyposis but resistance to transformation," *Nature*, 419:162-167, 2002.
Berdeaux et al., "SIK1 is a class II HDAC kinase that promotes survival of skeletal myocytes," *Nat Med*, 13:597-603, 2007.
Bild et al., "Multi-ethnic study of atherosclerosis:objectives and design," *Am J Epidemiol*, 156:871-881, 2002.
Boyle et al. "Annotation of functional variation in personal genomes using RegulomeDB," *Genome Res.*, 22(9):1790-1797, 2012.
Christensen et al., "Histone deacetylase (HDAC) inhibition as a novel treatment for diabetes mellitus," *Mol Med.*, 17(5-6):378-390, 2011.
Clark et al., "Phosphorylation of CRTC3 by the salt-inducible kinases controls the interconversion of classically activated and regulatory macrophages," *Proc Natl Acad Sci USA*, 109:16986-16991, 2012.
Hayden and Ghosh, "Shared principles in NF-kappaB signaling," *Cell*, 132:344-362, 2008.
Hong et al., "Interleukin-10 prevents diet-induced insulin resistance by attenuating macrophage and cytokine response in skeletal muscle," *Diabetes*, 58:2525-2535, 2009.
Hotamisligil, "Inflammation and metabolic disorders," *Nature*, 444:860-867, 2006.
Koo et al., "The CREB coactivator TORC2 is a key regulator of fasting glucose metabolism," *Nature*, 437:1109-1111, 2005.
Liao et al., "Krüppel-like factor 4 regulates macrophage polarization," *J Clin Invest*, 121:2736-2749, 2011.
Luan et al., "Leptin-mediated increases in catecholamine signaling reduce adipose tissue inflammation via activation of macrophage HDAC4," *Cell Metab.*, 19(6):1058-1065, 2014.
MacKenzie et al., "PGE$_2$ induces macrophage IL-10 production and a regulatory-like phenotype via a protein kinase A-SIK-CRTC3 pathway," *J Immunol*, 190:565-577, 2013.

(Continued)

*Primary Examiner* — Padma V Baskar
(74) *Attorney, Agent, or Firm* — Parker Highlander PLLC

(57) ABSTRACT

In some aspects, methods for treating a bacterial infection in a mammalian subject are provided. In some embodiments, a class IIa HDAC inhibitor such as, e.g., a HDAC4 inhibitor, may be used to treat a bacterial infection such as, e.g., anthrax, pertussis, tuberculosis, or cholera.

13 Claims, 12 Drawing Sheets

(56) References Cited

OTHER PUBLICATIONS

Mai et al., "Class II (IIa)-selective histone deacetylase inhibitors. 1. Synthesis and biological evaluation of novel (aryloxopropenyl)pyrrolyl hydroxyamides," *J Med Chem.*, 48(9):3344-3353, 2005.

Mai et al., "Identification of two new synthetic histone deacetylase inhibitors that modulate globin gene expression in erythroid cells from healthy donors and patients with thalassemia," *Mol Pharmacol.*, 72(5):1111-1123, 2007.

Marek et al, "Histone deacetylase (HDAC) inhibitors with a novel connecting unit linker region reveal a selectivity profile for HDAC4 and HDAC5 with improved activity against chemoresistant cancer cells," *J. Med. Chem.*, 56(2):427-36, 2013.

Marks and Breslow, "Dimethyl sulfoxide to vorinostat: development of this histone deacetylase inhibitor as an anticancer drug," *Nat. Biotechnol.*, 25(1):84-90, 2007.

Mihaylova et al., "Class IIa histone deacetylases are hormone-activated regulators of FOXO and mammalian glucose homeostasis," *Cell*, 145:607-621, 2011.

Mombelli et al., "Histone deacetylase inhibitors impair antibacterial defenses of macrophages," *J Infect Dis.*, 204(9):1367-1374, 2011.

Nebbioso et al., "Selective class II HDAC inhibitors may impaor myogenesis by modulating the stability and activity of HDAC-MEF2 complexes," *EMBO J.*, 10:776-782, 2009.

Nguyen et al., "Alternatively activated macrophages produce catecholamines to sustain adaptive thermogenesis," *Nature*, 480:104-108, 2011.

PCT International Search Report and Written Opinion issued in International Application No. PCT/US2015/025072, mailed Jun. 25, 2015.

Phiel et al., "Histone deacetylase is a direct target of valproic acid, a potent anticonvulsant, mood stabilizer, and teratogen," *J Biol Chem.*, 276(39):36734-36741, 2001.

Potthoff et al., "Histone deacetylase degradation and MEF2 activation promote the formation of slow-twitch myofibers," *J Clin Invest*, 117:2459-2467, 2007.

Qing et al., "Valproic acid inhibits Aβ production, neuritic plaque formation, and behavioural defects in Alzheimer's disease mouse models," *J Exp Med.*, 205(12):2781-2789, 2008.

Raqib et al., "Efficacy of sodium butyrate adjunct therapy in shigellosis: a randomized, double-blind, placebo-controlled clinical trial," *BMC Infectious Diseases*, 12(1):111, 2012.

Schug et al., "Myeloid deletion of SIRT1 induces inflammatory signaling in response to environmental stress," *Mol Cell Biol*, 30:4712-4721, 2010.

Song et al., "CRTC3 Links Catecholamine Signaling to Energy Balance," *Nature*, 468:933-939, 2010.

Takeda and Akira, "TLR signaling pathways," *Seminars in Immunology*, 16(1): 3-9, 2004.

Tang and Guo, "The adenylyl cyclase activity of anthrax edema factor," *Molecular Aspects of Medicine*, 30:423-430, 2009.

Uebi et al., "Involvement of SIK3 in glucose and lipid homeostasis in mice," *PLoS ONE*, 7:e37803, 2012.

Vega et al., "Histone deacetylase 4 controls chondrocyte hypertrophy during skeletogenesis," *Cell*, 119:555-566, 2004.

Wang et al., "A hormone-dependent module regulating energy balance," *Cell*, 145:596-606, 2011.

Williams et al., "Haploinsufficiency of *HDAC4* causes brachydactyly mental retardation syndrome, with brachydactyly type E, developmental delays, and behavioral problems," *Am J Hum Genet.*, 87(2):219-228, 2010.

Yedery et al., "Augmentation of cationic antimicrobial peptide production with histone deacetylase inhibitors as a novel epigenetic therapy for bacterial infections," *Antibiotics*, 4(1):44-61, 2015.

Yoshida et al., "Potent and specific inhibition of mammalian histone deacetylase both in vivo and in vitro by trichostatin A," *J. Biol. Chem.*, 265:17174-17179, 1990.

Yuan et al., "Reversal of obesity- and diet-induced insulin resistance with salicylates or targeted disruption of Ikkbeta," *Science*, 293:1673-1677, 2001.

Licciardi and Karagiannis, "Regulation of immune responses by histone deacetylase inhibitors," *ISRN Hematology*, 2012:690901, 10 pages, 2012.

Ozanne et al., "The clinically approved drugs dasatinib and bosutinib induce anti-inflammaotry macrophages by inhibiting the salt-inducible kinase," *Biochem J.*, 465:271-279, 2015.

Roger et al., "Histone deacetylase inhibitors impair innate immune responses to Toll-like receptor agonists and to infection," *Blood*, 117(4):1205-1217, 2011.

\* cited by examiner

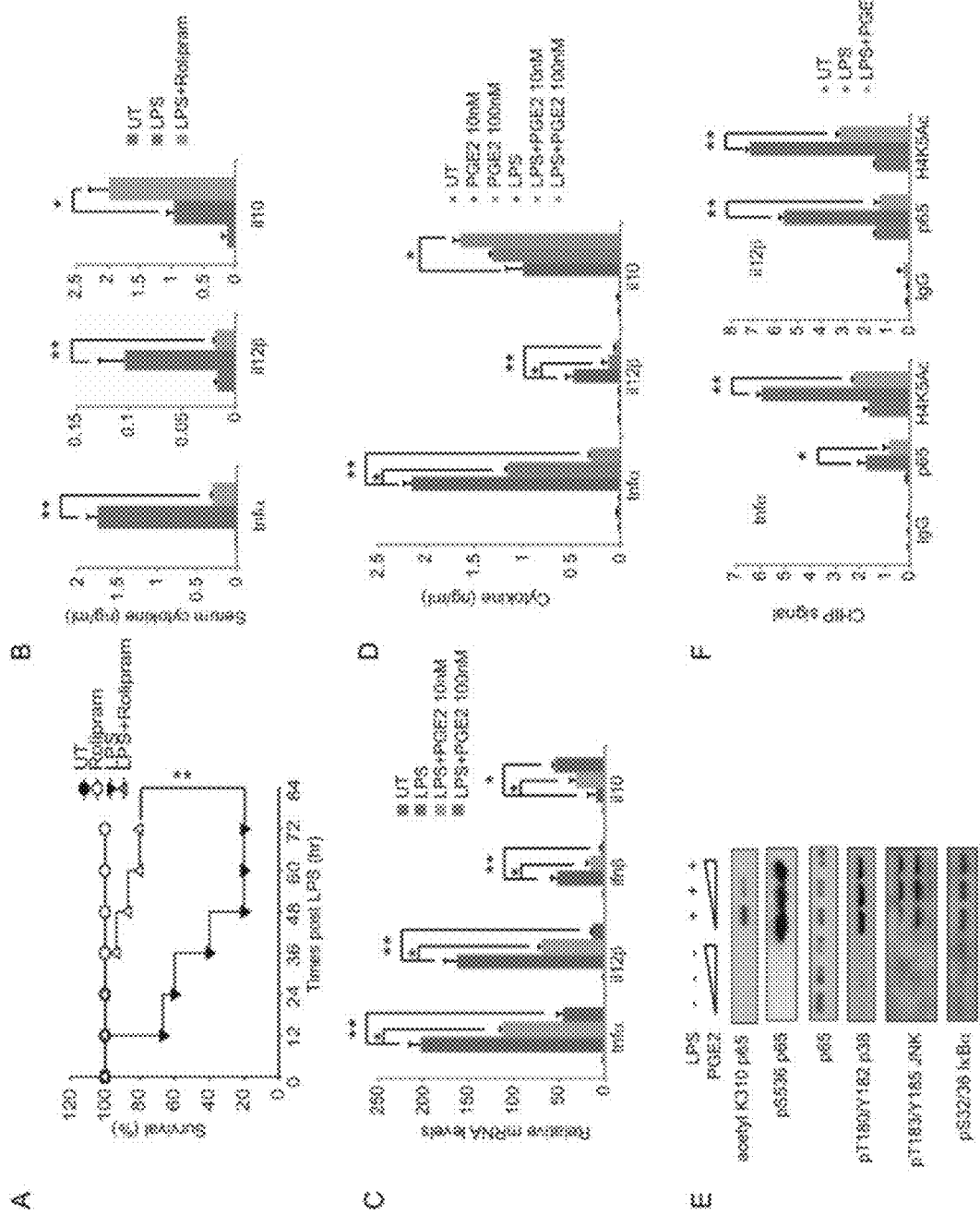
FIGS. 1A-F

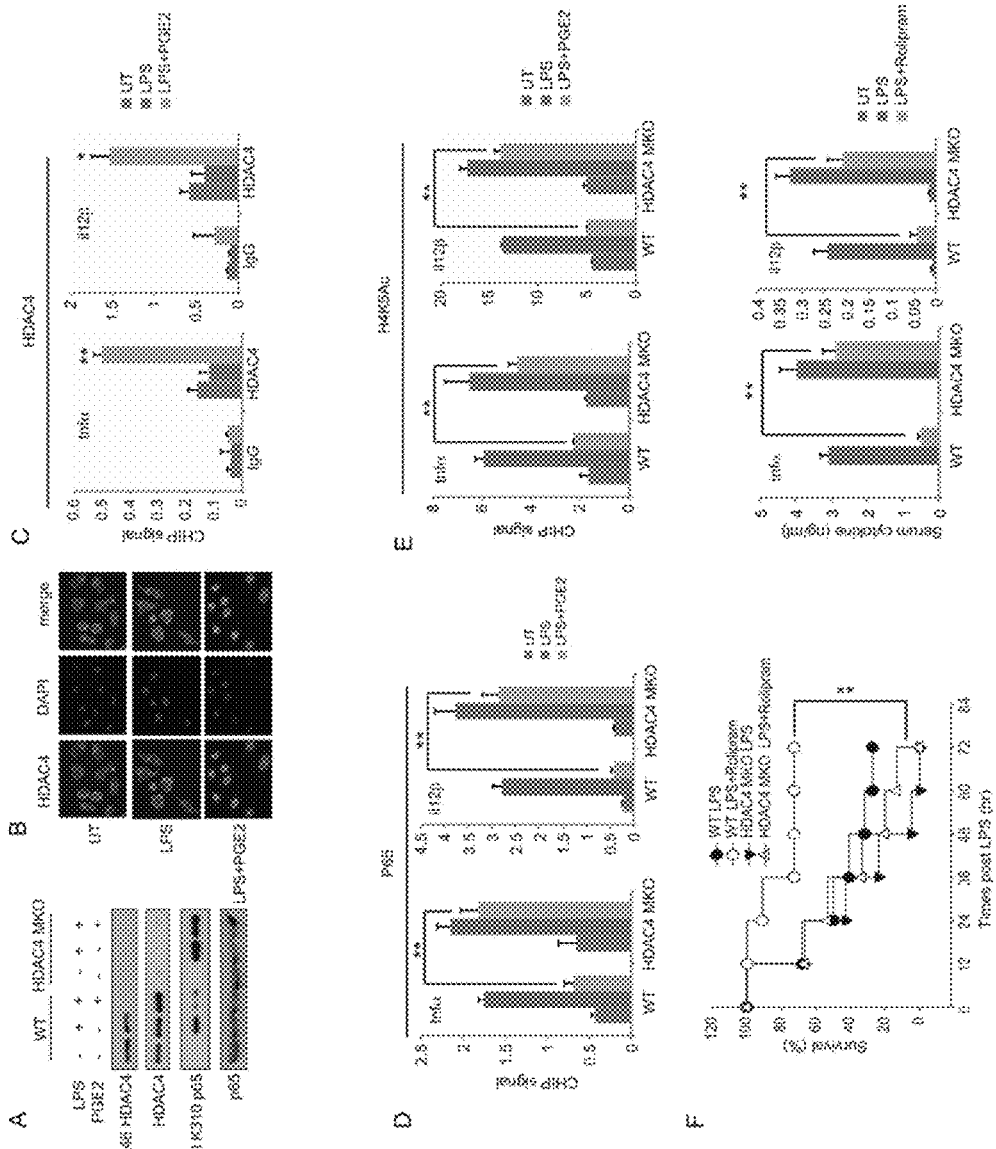
FIGS. 2A-F

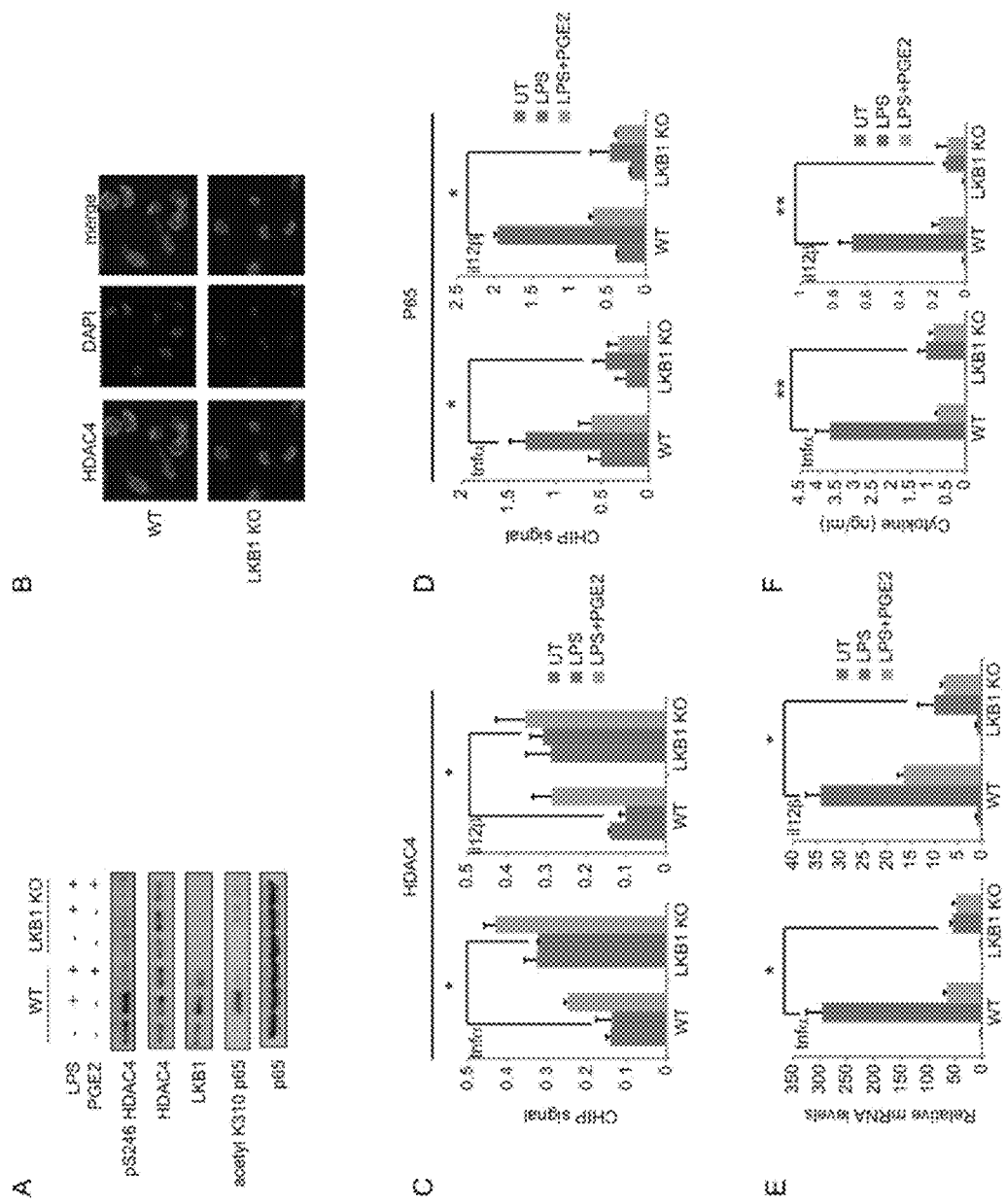
FIGS. 3A-F

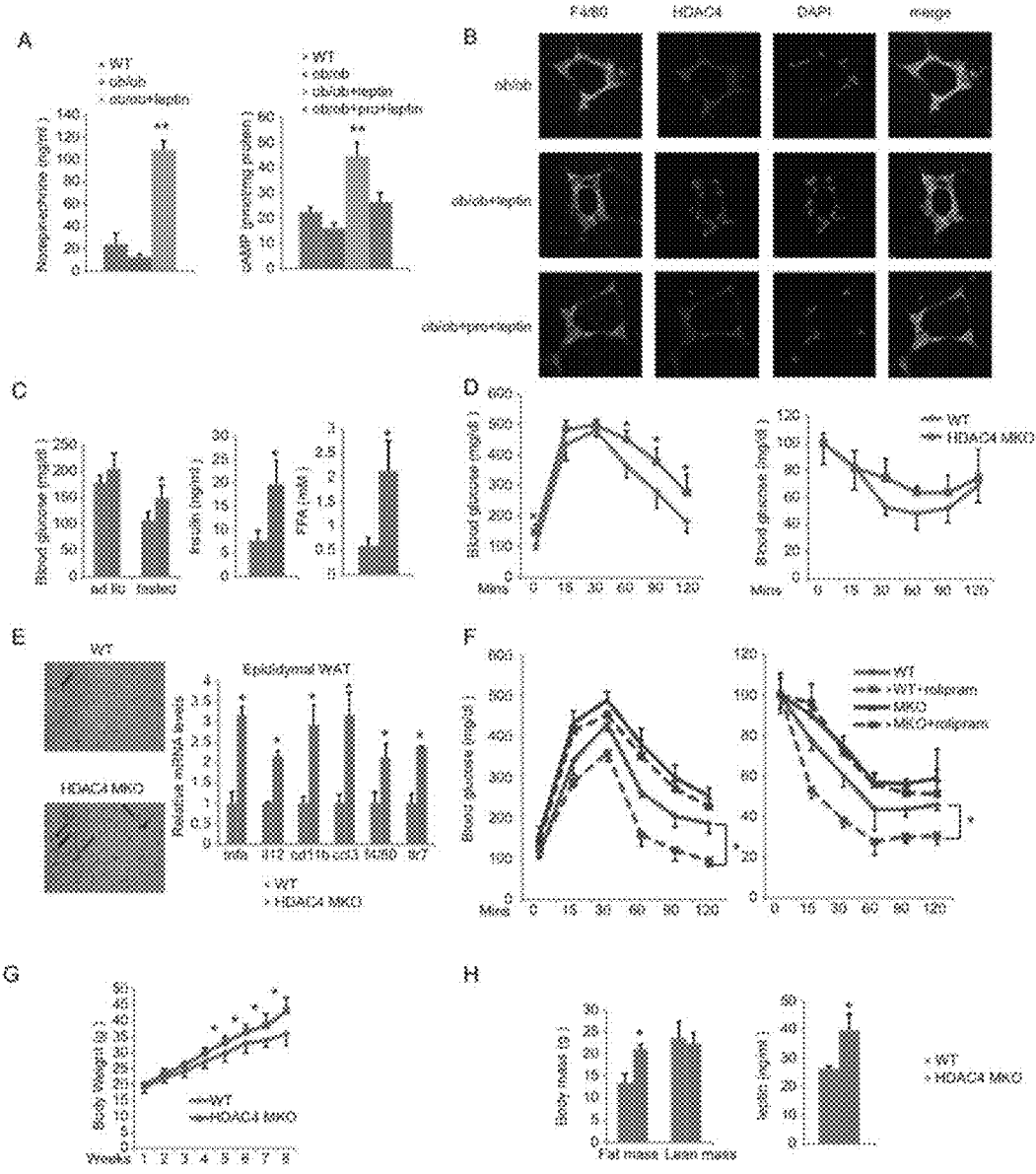
FIGS. 4A-H

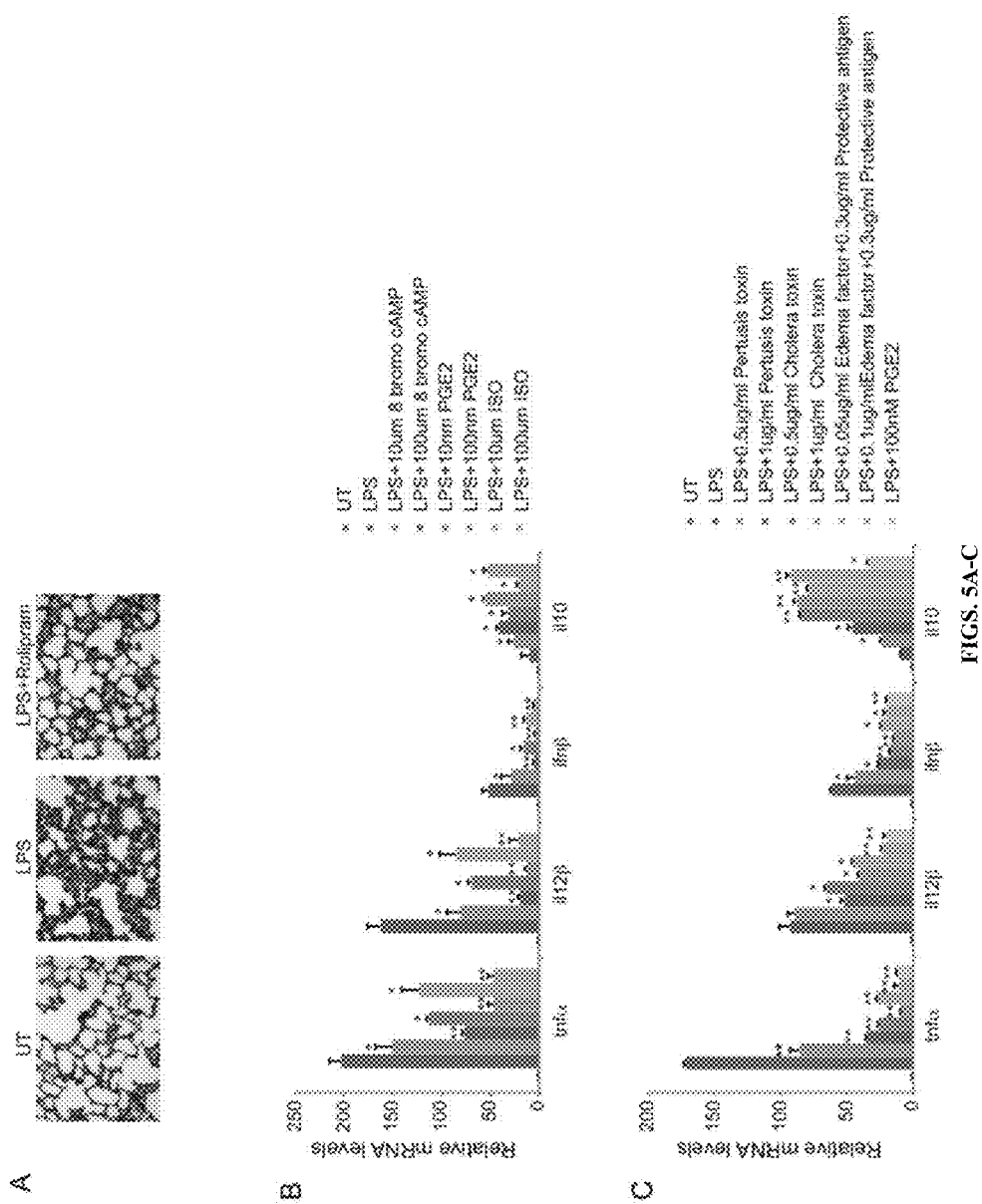
FIGS. 5A-C

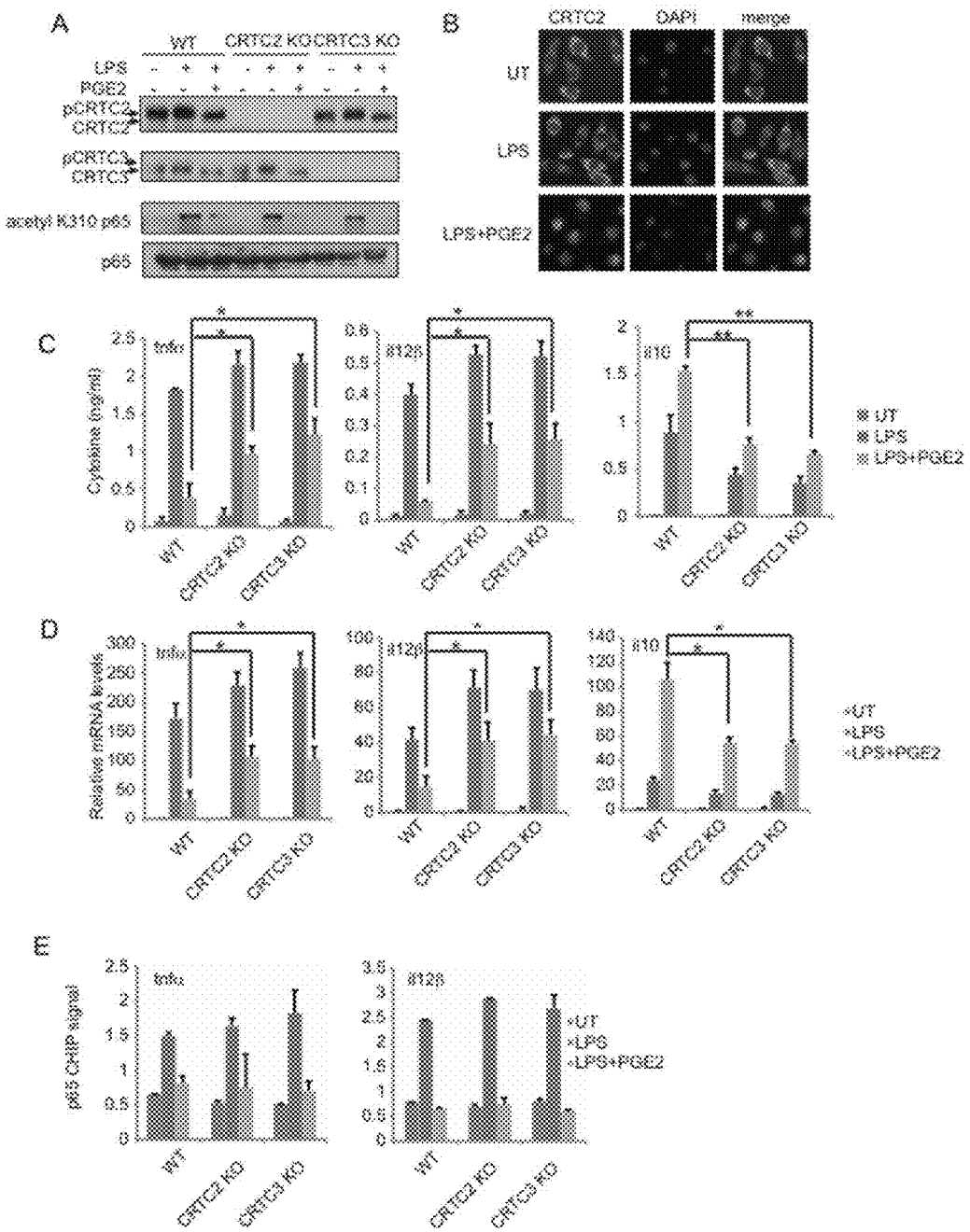
FIGS. 6A-E

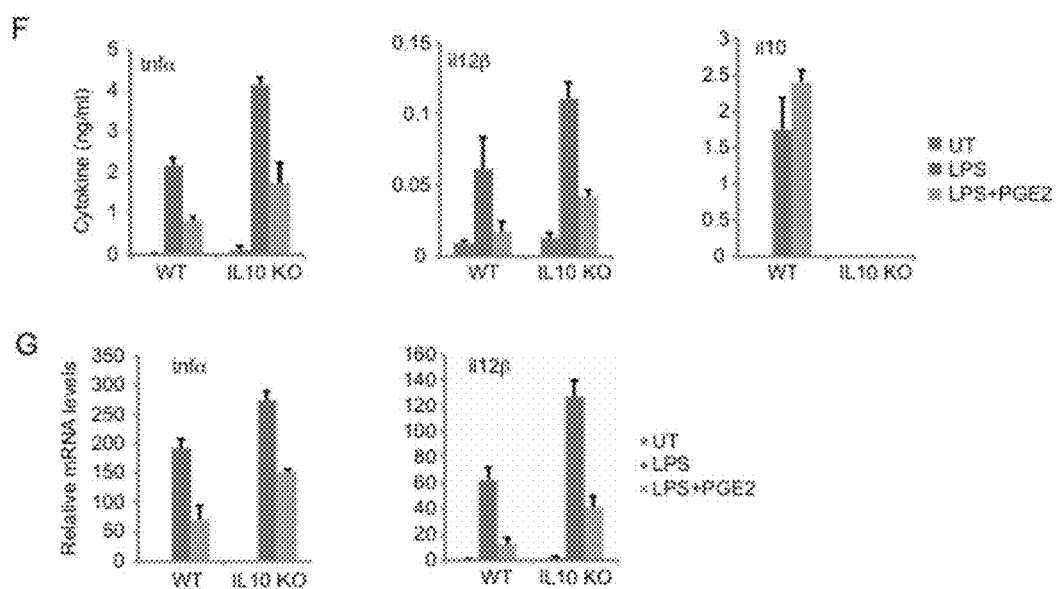
FIGS. 6F-G

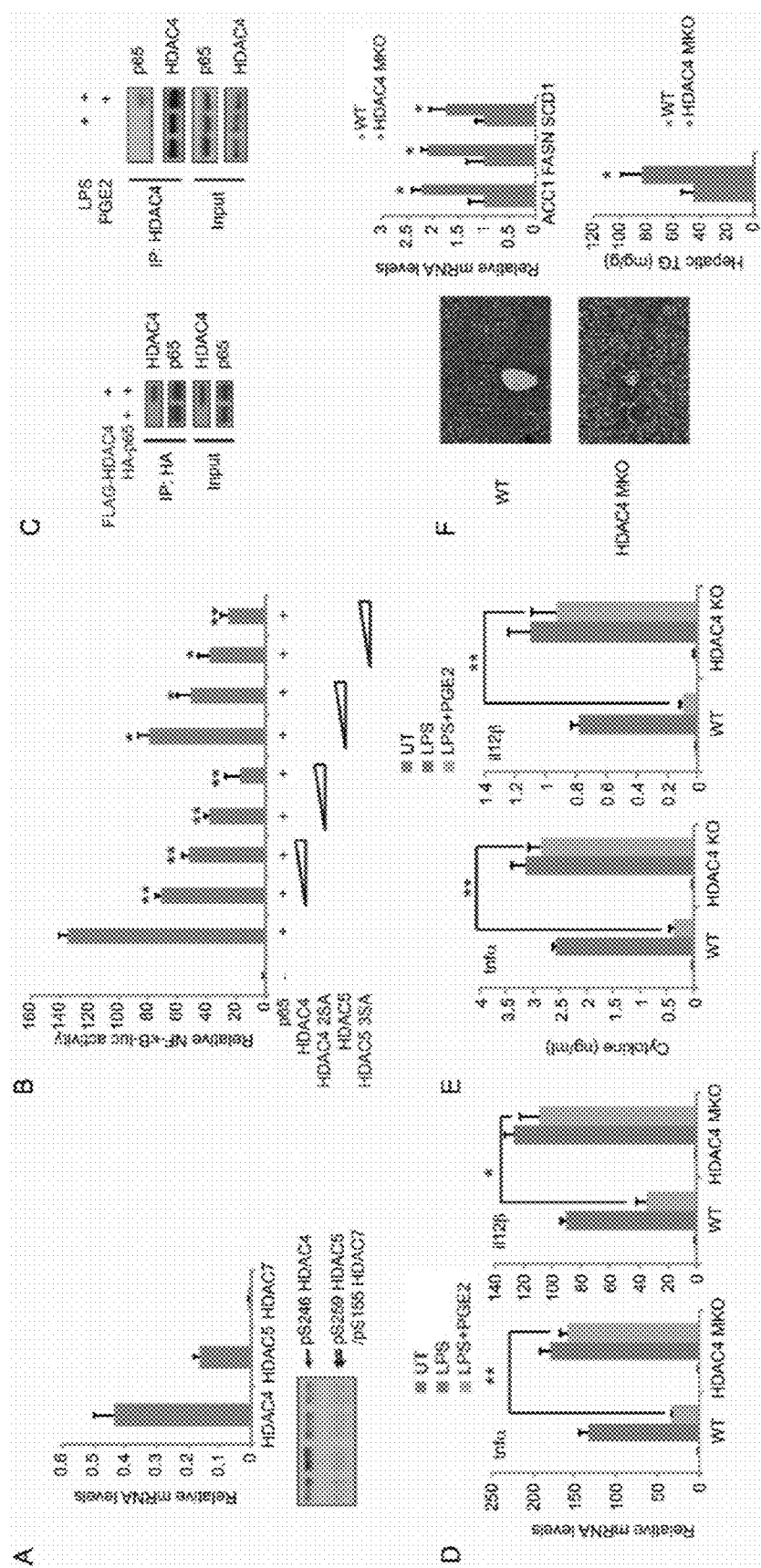
FIGS. 7A-F

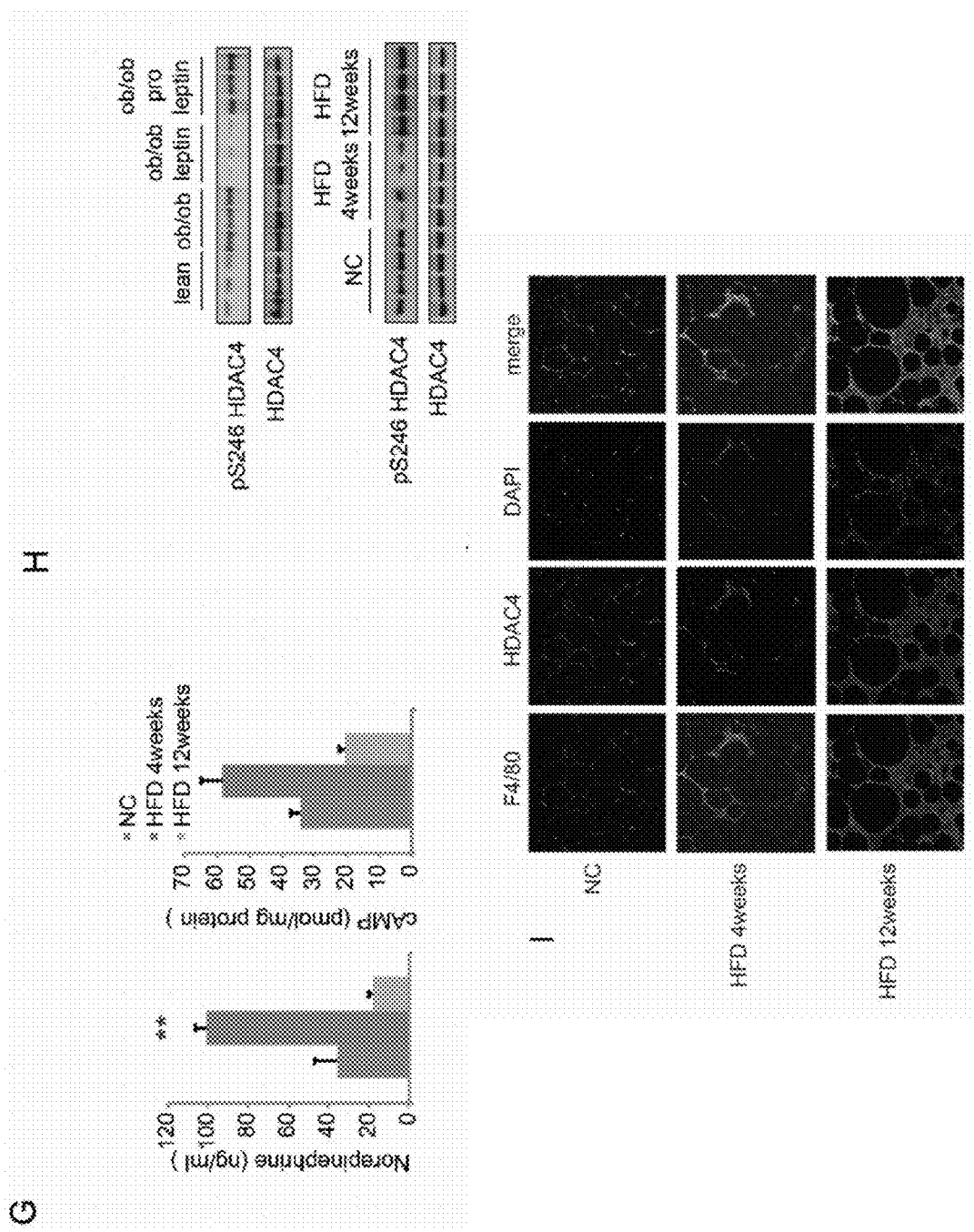
FIGS. 7G-I

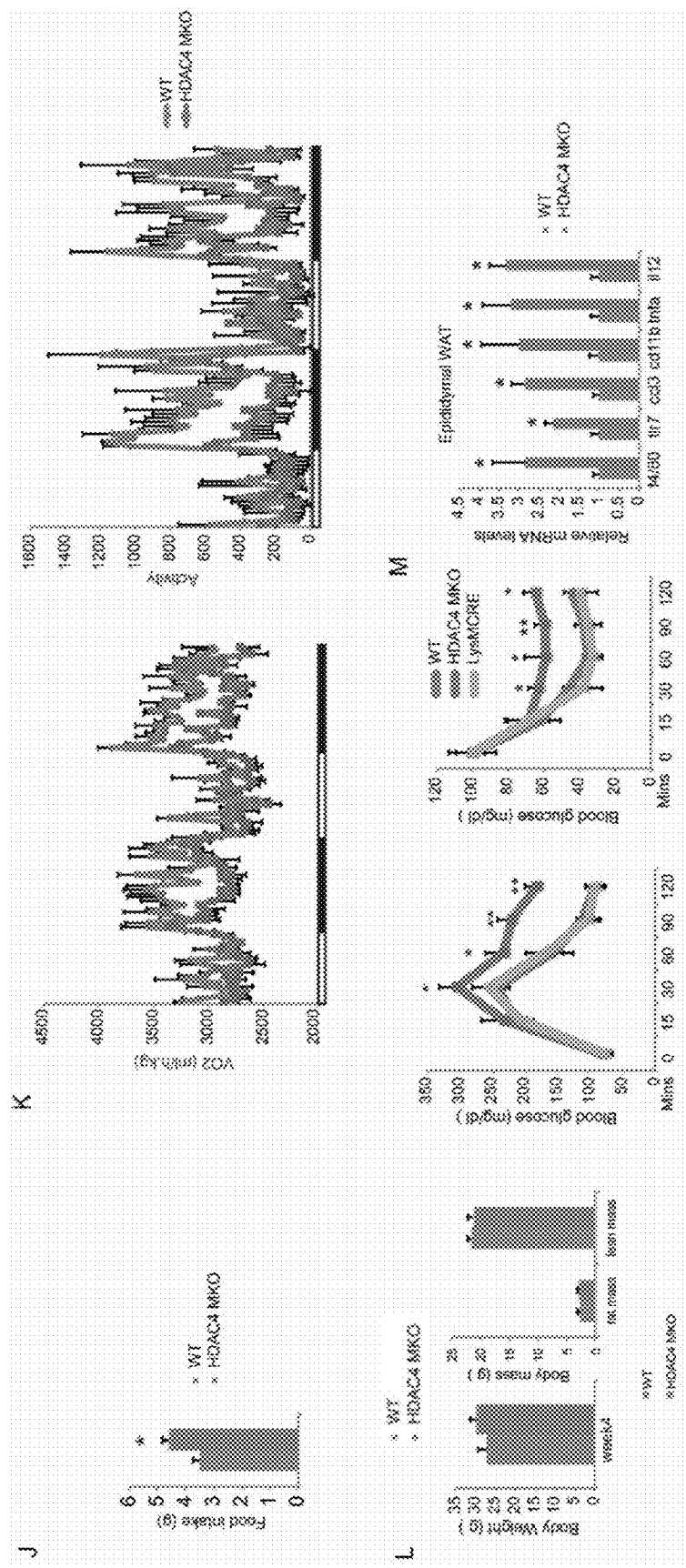
FIGS. 7J-M

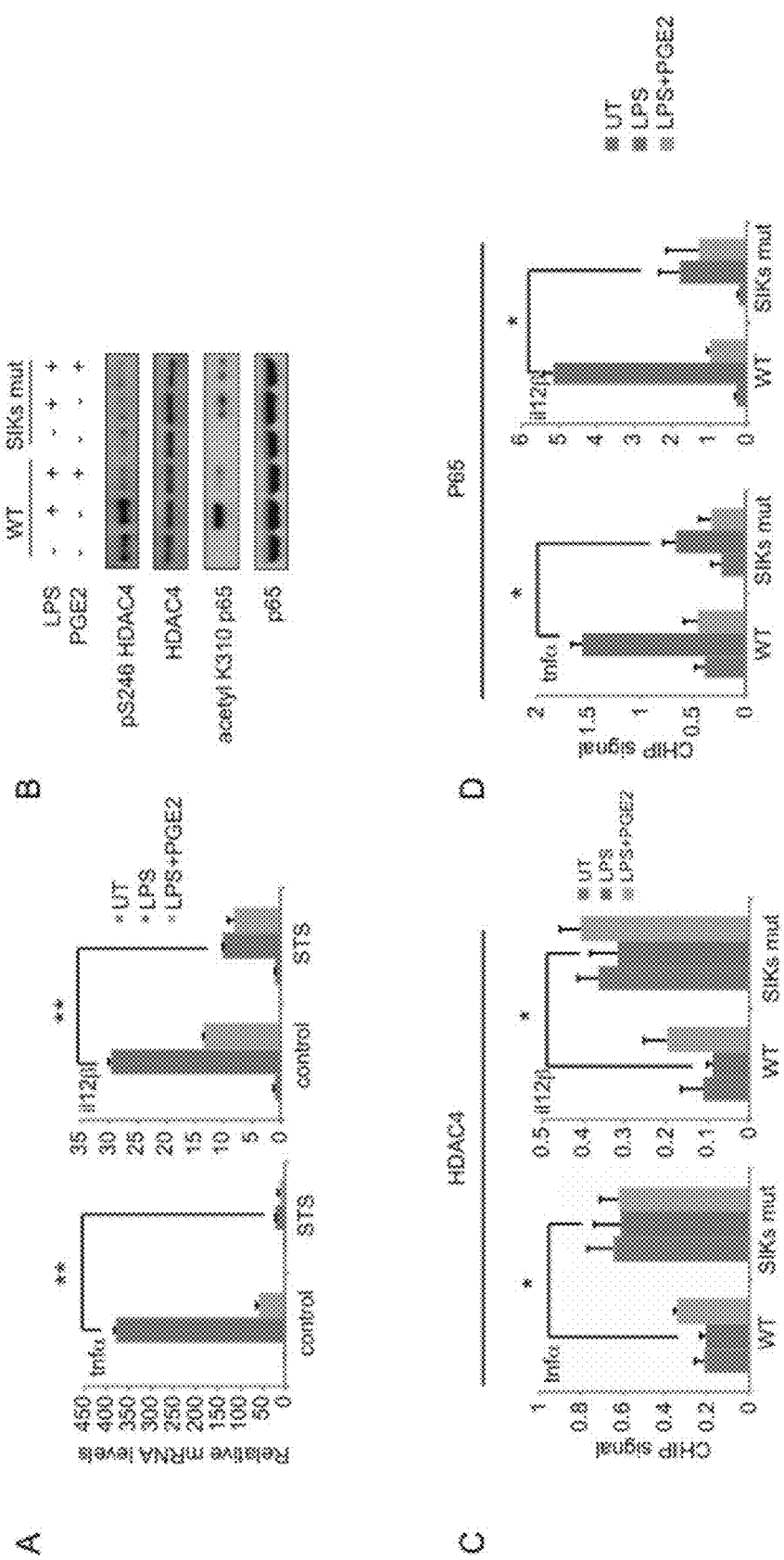
FIGS. 8A-D

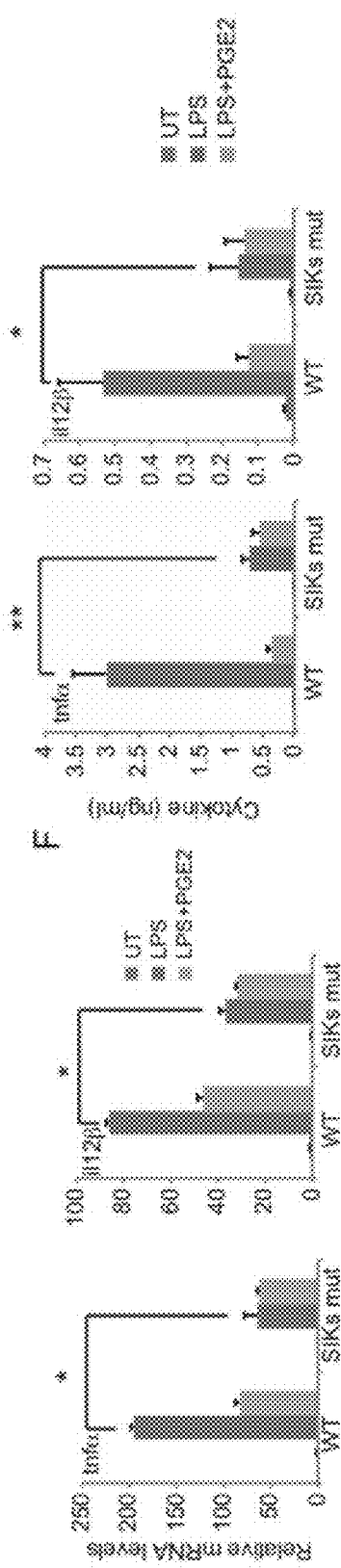
FIGS. 8E-F

SEQUENCE LISTING

```
<160> NUMBER OF SEQ ID NOS: 34

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
tgaacttcgg ggtgatcggt c                                        21

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
agccttgtcc cttgaagagg ac                                       22

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
gtagaggtgg actggactcc                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gcagacagag acgccattcc                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ggacaacata ctgctaaccg                                          20

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic Primer

<400> SEQUENCE: 6
ttcatggcct tgtagacacc                                               20

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
tccaagaaag gacgaacatt cg                                            22

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
tgaggacatc tcccacgtca a                                             21

<210> SEQ ID NO 9
<211> LENGTH: 19
<212> TYPE: DNA
<213> ORGANISM: Artificial Sequence
<220> FEATURE:
<223> OTHER INFORMATION: Synthetic Primer

<400> SEQUENCE: 9
ctgcaagtgg cccctacag                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
ctgctcatgt tgacgctgga                                               20

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
tgcagcacgt tttgctcct                                                19

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gacagctccc cagttttggt                                               20
```

-continued

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
ggcaggctta caccagcaa                                            19

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
tgggcaggct gtagggaata                                           20

<210> SEQ ID NO 15
<211> LENGTH: 23
<212> TYPE: DNA
<213> ORGANISM: Artificial Sequence
<220> FEATURE:
<223> OTHER INFORMATION: Synthetic Primer

<400> SEQUENCE: 15
ttctctgtac catgacactc tgc                                       23

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
cgtggaatct tccggctgta g                                         21

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
tgactcacct tgtggtccta a                                         21

<210> SEQ ID NO 18
<211> LENGTH: 22
<212> TYPE: DNA
<213> ORGANISM: Artificial Sequence
<220> FEATURE:
<223> OTHER INFORMATION: Synthetic Primer

<400> SEQUENCE: 18
cttcccagaa tccagtcttt cc                                        22

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
atggacgctg atggcaatac c                                      21

<210> SEQ ID NO 20
<211> LENGTH: 19
<212> TYPE: DNA
<213> ORGANISM: Artificial Sequence
<220> FEATURE:
<223> OTHER INFORMATION: Synthetic Primer

<400> SEQUENCE: 20
tccccattca cgtctccca                                          19

<210> SEQ ID NO 21
<211> LENGTH: 21
<212> TYPE: DNA
<213> ORGANISM: Artificial Sequence
<220> FEATURE:
<223> OTHER INFORMATION: Synthetic Primer

<400> SEQUENCE: 21
atgtggacac ggaagagaca a                                       21

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
ggtaagggta agattggtgg tg                                      22

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer

<400> SEQUENCE: 23
aacatcgaag aggacttccg a                                       21

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
caagcgttca cctgagatga c                                       21

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
ggaggtggtg atagccggta t                                       21

```
<210> SEQ ID NO 26
<211> LENGTH: 21
<212> TYPE: DNA
<213> ORGANISM: Artificial Sequence
<220> FEATURE:
<223> OTHER INFORMATION: Synthetic Primer

<400> SEQUENCE: 26
tgggtaatcc atagagccca g                                             21

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
gatgaaccat ctccgttggc                                               20

<210> SEQ ID NO 28
<211> LENGTH: 23
<212> TYPE: DNA
<213> ORGANISM: Artificial Sequence
<220> FEATURE:
<223> OTHER INFORMATION: Synthetic Primer

<400> SEQUENCE: 28
gacccaatta tgaatcggga gtg                                           23

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer

<400> SEQUENCE: 29
ttcttgcgat acactctggt gc                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic Primer

<400> SEQUENCE: 30
cgggattgaa tgttcttgtc gt                                            22

<210> SEQ ID NO 31
<211> LENGTH: 21
<212> TYPE: DNA
<213> ORGANISM: Artificial Sequence
<220> FEATURE:
<223> OTHER INFORMATION: Synthetic Primer

<400> SEQUENCE: 31
agtatctctg cctccttcct t                                             21

<210> SEQ ID NO 32
<211> LENGTH: 21
<212> TYPE: DNA
<213> ORGANISM: Artificial Sequence
<220> FEATURE:
<223> OTHER INFORMATION: Synthetic Primer
```

```
<400> SEQUENCE: 32
gcaacactga aaactagtgt c                                          21

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
ccccagattg ccacagaatc                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
ccagtgagtg aaagggacag                                            20
```

CLASS IIA HDAC INHIBITORS FOR THE TREATMENT OF INFECTION

This application claims the benefit of U.S. Provisional Patent Application No. 61/977,481, filed Apr. 9, 2014, the entirety of which is incorporated herein by reference.

The invention was made with government support under Grant Nos. R01-DK049777, R01-DK083834, R01-DK091618, R01-DK079888, and R01-HL071205 awarded by the National Institutes of Health, Grant Nos. N01 HC-95159, N01-HC-95160, N01-HC-95161, N01-HC-95162, N01-HC-95163, N01-HC-95164, N01-HC-95165, N01-HC-95166, N01-HC-95167, N01-HC-95168, N01-HC-95169 and RR-024156 awarded by National Heart, Lung, and Blood Institute (NHLBI), Grant No. N02-HL-6-4278 from NHLBI, and Grant No. P30-DK063491 awarded by the National Institute of Diabetes and Digestive and Kidney Disease Diabetes Research Center (DRC). The government has certain rights in the invention.

BACKGROUND OF THE INVENTION

1. Field of the Invention

The present invention relates generally to the field of molecular biology and medicine. More particularly, it concerns treatments for bacterial infections.

2. Description of Related Art

Obesity is associated with a chronic inflammatory state that contributes to the development of insulin resistance (Hotamisligil, 2006). Activation of the Inhibitor of Kappa B kinase β (IKKβ) in macrophages stimulates the release of inflammatory mediators that promote insulin resistance (Arkan et al., 2005; Yuan et al., 2001); indeed, disruption of NF-κB activity through deletion of IKKβ increases insulin sensitivity (Arkan et al., 2005).

The second messenger cAMP has been found to exert potent anti-inflammatory effects on macrophage function through induction of the Ser/Thr kinase PKA (Aronoff et al., 2005). A number of bacteria including *Mycobacterium tuberculosis* (Agarwal et al., 2009) and *Bacillus anthracis* (Tang and Guo, 2009) have been shown to evade the immune system by stimulating cAMP production. Clearly, there is a need for new therapies to treat an infection by bacteria that can evade or suppress immune destruction by stimulating cAMP production in the host.

SUMMARY OF THE INVENTION

The present invention overcomes limitations in the prior art by providing methods and pharmaceutical preparations for the treatment of a bacterial infection in a subject such as a human patient. In some embodiments, bacteria in said bacterial infection may evade immune destruction or suppress immune responses in the subject by stimulating cAMP production, e.g., in macrophages of the subject. In some aspects, a class IIa HDAC inhibitor such as, e.g., a HDAC-4 inhibitor, may be used to treat a bacterial infection in a mammalian subject such as a human patient.

An aspect of the present invention relates to a method of treating a bacterial infection in a mammalian subject in need thereof, comprising administering to the subject a therapeutically effective dose of a class IIa HDAC inhibitor to the subject. In some embodiments, bacteria in said bacterial infection secrete a toxin that increases or stimulates production of cAMP the subject. The toxin may promote or cause cAMP production in macrophages in said subject. In some embodiments, the bacterial infection promotes or causes cAMP production in macrophages in said subject. The bacterial infection may comprise or consist of infection by anthrax (*Bacillus anthracis*), tuberculosis (*Mycobacterium tuberculosis*), pertussis (*Bordetella pertussis*), or cholera (*Vibrio cholerae*). In some embodiments, the class IIa HDAC inhibitor is valproic acid (sodium 2-propylpentanoate), Trichostatin A ((2E,4E,6R)-7-(4-(Dimethylamino)phenyl)-N-hydroxy-4,6-dimethyl-7-oxo-2,4-heptadienamide), LMK235 (N-[[6-(Hydroxyamino)-6-oxohexyl]oxy]-3,5-dimethylbenzamide), MC1568 (3-[5-(3-(3-Fluorophenyl)-3-oxopropen-1-yl)-1-methyl-1H-pyrrol-2-yl]-N-hydroxy-2-propenamide), or SAHA (N-Hydroxy-N'-phenyloctanediamide). The class IIa HDAC inhibitor may selectively inhibit class IIa HDAC. In some embodiments, the class IIa HDAC inhibitor is MC1568 (3-[5-(3-(3-Fluorophenyl)-3-oxopropen-1-yl)-1-methyl-1H-pyrrol-2-yl]-N-hydroxy-2-propenamide). The class IIa HDAC inhibitor may selectively inhibit HDAC4. In some embodiments, the class IIa HDAC inhibitor is LMK235 (N-[[6-(Hydroxyamino)-6-oxohexyl]oxy]-3,5-dimethylbenzamide), MC1568 (3-[5-(3-(3-Fluorophenyl)-3-oxopropen-1-yl)-1-methyl-1H-pyrrol-2-yl]-N-hydroxy-2-propenamide), or Trichostatin A ((2E,4E,6R)-7-(4-(Dimethylamino)phenyl)-N-hydroxy-4,6-dimethyl-7-oxo-2,4-heptadienamide). The class IIa HDAC inhibitor may be comprised in a pharmaceutical preparation comprising an excipient. The pharmaceutical preparation may be formulated for oral, intravenous, or parenteral administration. In some embodiments, the method further comprises administering a second antibacterial therapy to the subject. The second antibacterial therapy may comprise or consist of administering an antibiotic to the subject. The antibiotic may be ciprofloxacin, doxycycline, erythromycin, vancomycin, penicillin, streptomycin, bedaquiline, delamanid, erythromycin, azithromycin, or trimethoprim-sulfamethoxazole (TMP-SMZ). The second antibacterial therapy may comprise administering an antibody to the subject. The antibody may be a monoclonal and/or humanized antibody. In some embodiments, the antibody is raxibacumab. In some embodiments, the method is further defined as a method of promoting or increasing macrophage killing or recognition of the bacterial infection in the subject. The subject may be a human.

Another aspect of the present invention relates to a pharmaceutical preparation comprising a class II HDAC inhibitor for the treatment of a bacterial infection in a subject. The bacterial infection may comprise or consist of infection by anthrax (*Bacillus anthracis*), tuberculosis (*Mycobacterium tuberculosis*), pertussis (*Bordetella pertussis*), or cholera (*Vibrio cholerae*). In some embodiments, the class IIa HDAC inhibitor is valproic acid (sodium 2-propylpentanoate), Trichostatin A ((2E,4E,6R)-7-(4-(Dimethylamino)phenyl)-N-hydroxy-4,6-dimethyl-7-oxo-2,4-heptadienamide), LMK235 (N-[[6-(Hydroxyamino)-6-oxohexyl]oxy]-3,5-dimethylbenzamide), MC1568 (3-[5-(3-(3-Fluorophenyl)-3-oxopropen-1-yl)-1-methyl-1H-pyrrol-2-yl]-N-hydroxy-2-propenamide), or SAHA (N-Hydroxy-N-phenyloctanediamide).

Yet another aspect of the present invention relates to a method for testing for an increased risk of obesity or type II diabetes in a human subject comprising testing for the presence or absence of a single nucleotide polymorphism (SNP) in the human subject selected from Table 3 or Table 4, wherein if the human subject has the SNP, then the human subject has an increased risk of obesity or type II diabetes. The testing to determine the presence or absence of the SNP may be preformed by a variety of methods as would be known to one of skill. For example, the presence or absence of the SNP may be identified via a method comprising or consisting of polymerase chain reaction (PCR), DNA sequencing, cDNA sequencing, RNA sequencing, next generation sequencing, detection with a molecular beacon, etc. The human subject may be, e.g., of Caucasian, African, or Chinese descent.

In yet another aspect an activator of HDAC4 may be administered to a subject to reduce inflammation or decrease insulin resistance. The activator of HDAC4 may be comprised in a pharmaceutical composition comprising an excipient. The HDAC4 activator may be, e.g., ITSA1 (N-(1H-Benzotriazol-1-yl)-2,4-dichlorobenzamide) or romidepsin (also referred to as depsipeptide, istodax, or chromadax). The subject may be a mammal such as, e.g., a mouse, rat, primate, monkey, etc. Preferably, the subject is a human patient.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-F: Anti-inflammatory effects of cAMP in macrophages. Effect of LPS i.p. (30 mg/kg) on survival (FIG. 1A) and circulating cytokine concentrations (FIG. 1B) in 12 week old C57B1/6J mice. Co-injection of phospho-diesterase inhibitor rolipram (5 mg/kg) indicated. (n=8: for this and other figures *P<0.05: **P<0.01). Effect of PGE2 on cytokine mRNA amounts (FIG. 1C) and protein secretion (FIG. 1D) from Bone Marrow Macrophages (BMMs) treated with LPS. FIG. 1E, Effect of PGE2 on LPS-induced increases in JNK or P38 activation, IκB phosphorylation, and on p65 acetylation. Co-treatment with increasing concentrations of PGE2 indicated. FIG. 1F, Chromatin immunoprecipitation (ChIP) assay of p65 recruitment and histone H4K5 acetylation over TNFα and IL12β promoters in BMMs exposed to LPS and PGE2. For bar graphs shown in this figure and for bar graphs described in the figures listed below, the individual bars listed in each group from left to right of a given bar graph correspond with the groups shown in the legend from top to bottom; for example, in FIG. 1B, the results shown in the tnfα bar graph correspond with, from left to right: UT, LPS, and LPS+rolipram, where a statistically significant difference is shown between the LPS and LPS+rolipram groups in the tnfα bar graph.

FIGS. 2A-F: Class IIa HDACs inhibit cytokine gene expression in response to cAMP. Effect of LPS and PGE2 on HDAC4 de-phosphorylation (FIG. 2A) and cellular localization (FIG. 2B). FIG. 2A, Phospho (Ser246) HDAC4 amounts in control (HDAC4 fl/fl) and HDAC4 MKO cells exposed to LPS and PGE2. Amounts of acetylated and total p65 in wild-type and HDAC4 MKO BMMs exposed to LPS plus PGE2 indicated. FIG. 2B, HDAC4 subcellular localization in BMMs exposed to LPS and PGE2. FIG. 2C, ChIP assay showing effects of PGE2 and LPS on HDAC4 recruitment to TNFα or IL12β promoters. Effect of LPS and PGE2 on p65 occupancy (FIG. 2D) and histone H4K5 acetylation over TNFα and IL12β promoters (FIG. 2E) in BMMs from HDAC4 MKO or control littermates. FIG. 2F, Effect of LPS and rolipram administration on survival (left) and circulating cytokine concentrations (right) in control or HDAC4 MKO mice (n=12). The legend in FIG. 3D also applies to FIG. 3C. Similarly, the legend for FIG. 3F also applies to FIG. 3E.

FIGS. 3A-F: LKB1 regulates cytokine gene expression by modulating HDAC4 phosphorylation. Effect of LPS and PGE2 on HDAC4 de-phosphorylation (FIG. 3A) and nuclear localization (FIG. 3B) in control (LKB1 fl/fl) and LKB1 KO BMMs. FIG. 3A, Phospho (S246) HDAC4 protein amounts in LKB1 KO cells. Amounts of acetylated and total p65 indicated. ChIP assays showing HDAC4 (FIG. 3C) and p65 recruitment (FIG. 3D) to TNFα and IL12β promoters in control or LKB1 KO BMMs. Cytokine mRNA amounts (FIG. 3E) and protein secretion (FIG. 3F) from BMMs exposed to LPS and PGE2 as indicated.

FIGS. 4A-H: Insulin resistance and obesity in HDAC4 MKO mice. FIG. 4A, Circulating norepinephine concentrations (left) and cAMP content in epididymal fat pads (right) of lean and ob/ob mice following intra-peritoneal (i.p.) injection with PBS or leptin (3 μg/g) for 2 hr (n=3). Effect of propranolol (1 μg/g) i.p. on cAMP content in leptin-treated mice (n=3). FIG. 4B, HDAC4 localization in adipose tissue macrophages of lean and ob/ob mice. Mice were pre-injected with propranolol (1 μg/g) or vehicle i.p. for 1 hr followed by leptin (3 μg/g) for 2 hr (n=3). Macrophages identified by co-staining with F4/80 antiserum. FIG. 4C, Circulating glucose, insulin, and free fatty acids in HDAC4 MKO compared to control littermates on a HFD for 8 weeks (n 8). FIG. 4D, Glucose and Insulin tolerance testing of HDAC4 MKO and control (HDAC4 fl/fl) mice on a HFD for 8 weeks (n=8). FIG. 4E, Macrophage infiltration in WAT by immunohistochemical (left) and Q-PCR (right) analyses. FIG. 4F, Effect of rolipram administration for 7 days on glucose and insulin tolerance in wild-type and HDAC4 MKO mice on a HFD for 12 weeks (n=6). Weight gain (FIG. 4G) (n=8) as well as fat mass (n=4) and circulating leptin levels (n=8) (FIG. 4H) in HDAC4 MKO and control littermates. For each of the conditions shown in bar graphs FIG. 4C, FIG. 4E, and FIG. 4H: data for wild-type (WT) mice is shown on the left and HDAC4 knockout mice (HDAC4 MKO) is shown on the right. Higher blood glucose levels were observed for HDAC4 MKO, as compared to WT mice, as shown in FIG. 4D and FIG. 4F. Heavier body weights were observed for HDAC4 MKO, as compared to WT mice, as shown in FIG. 4G.

FIGS. 5A-C: cAMP agonists inhibit cytokine gene expression. FIG. 5A, H&E staining of lung tissue from mice injected with LPS or LPS+ phospho-diesterase 4 inhibitor rolipram. FIG. 5B, Effect of co-treatment with LPS and cAMP agonist (8-Br-cAMP) or ligand for Gs coupled receptors (isoproterenol, PGE2) on cytokine (TNFα, IL12β, IFNβ, IL10) gene expression in BMMs. FIG. 5C, Effect of bacterial toxins (Pertussis, Cholera, Edema Factor) on LPS-dependent increases in cytokine gene expression in BMMs.

FIGS. 6A-G: CREB/CRTC pathway modulates the amplitude of cytokine gene expression via induction of IL10. FIG. 6A, Immunoblot of CRTC2 and CRTC3 phosphorylation and protein amounts in BMMs from wild-type (WT) and knockout (KO) mice. Effect of LPS and PGE2 on p65 acetylation in CRTC2−/− or CRTC3−/−BMMs also shown. FIG. 6B, Immunocytochemical analysis of CRTC2 localization in WT BMMs under basal conditions and following exposure to LPS or LPS plus PGE2 for 1 hour. FIG. 6C and FIG. 6D, Effect of LPS and PGE2 on cytokine secretion (FIG. 6C)(TNFα, IL12β, IL10) and cytokine mRNA amounts (FIG. 6D) from BMMs of CRTC2 and CRTC3 KO mice relative to WT littermates. E. ChIP assay showing effect of CRTC2 or CRTC3 KO on recruitment of p65 to cytokine promoters. F. and G. Effect of LPS and PGE2 on cytokine secretion (FIG. 6F) and gene expression (FIG. 6G) in BMMs from IL10 KO and WT mice.

FIGS. 7A-M: HDAC4 mediates cAMP-dependent inhibition of cytokine genes in macrophages. FIG. 7A, Relative expression of class IIa HDAC family members (HDAC4, HDAC5 and HDAC7) in BMMs by Q-PCR (top) and immunoblot (bottom) analysis. FIG. 7B, Transient assay of HEK293T cells showing NF-κB reporter activity in cells co-transfected with increasing amounts of WT or phosphorylationdefective HDAC4 (HDAC4, HDAC4 2SA) or HDAC5 (HDAC5, HDAC5 3SA). FIG. 7C, Interaction between p65 and HDAC4 in BMMs in response to PGE2 and LPS stimulation. Effect of LPS and PGE2 on mRNA amounts (FIG. 7D) and secretion (FIG. 7E) of TNFα and IL12β from BMMs of WT or HDAC4 MKO mice. FIG. 7F, Left, microscopic sections showing relative hepatic steatosis in HFD-fed HDAC4 MKO or WT mice. Right, Q-PCR analysis of mRNA amounts for lipogenic genes in livers of HDAC4 MKO mice (top). Bottom right, relative triglyceride amounts in livers of WT and HDAC4 MKO mice. FIG. 7G, Left, circulating norepinephrine concentrations in mice on normal chow (NC) or high fat diet (HFD) for 4 or 12 weeks (n=4 per group). Right, cAMP content in WAT from NC and HFD mice (n=4 per group). FIG. 7H, Top, Immunoblot showing effects of leptin on HDAC4 dephosphorylation in fat pads of ob/ob mice. Effect of β adrenergic antagonist (Propanolol) on HDAC4 dephosphorylation shown. Bottom, immunoblot showing effect of NC or HFD feeding for 4 or 12 weeks on de-phospho HDAC4 amounts in WAT. (n=4 per group). FIG. 7I, Immunohistochemical analysis of HDAC4 subcellular localization in adipose tissue macrophages of NC and HFD mice. Sections co-stained with macrophage-specific F4/80 antiserum (n=4 per group). Mice were fed a high fat diet for 4 or 12 weeks. J. and K. Metabolic cage analysis showing relative food intake (FIG. 7J) as well as oxygen consumption and physical activity (FIG. 7K) in WT versus HDAC4 MKO mice under HFD feeding conditions. The line for WT is shown above the line for HDAC4 MKO in FIG. 7K, although no sitatistically significant differences were observed. FIG. 7L, Left, Body weight and fat mass of HDAC4 MKO and control littermates fed a HFD for 4 weeks (n=6 per group). Right, Glucose and Insulin tolerance testing of HDAC4 MKO, WT (HDAC4 fl/fl) mice as well as LysMCRE mice fed on HFD for 4 weeks (n=6 per group). FIG. 7M, Relative macrophage infiltration in WAT from HDAC4 MKO and control littermates fed on HFD for 4 weeks by Q-PCR analyses. As shown in FIG. 7M, blood glucose levels were higher in HDAC4 MKO, as compared to WT or LysMCRE.

FIGS. 8A-F: SIKs regulates cytokine gene expression by modulating HDAC4 phosphorylation. FIG. 8A, Effect of pre-treatment with SIK inhibitor staurosporine (STS; 10 nM) on LPS mediated induction of cytokine genes in BMMs. Cells were treated with LPS or LPS plus PGE2 for 2 hours. FIG. 8B, Effect of LPS and PGE2 on HDAC4 de-phosphorylation in WT and SIKs Mut BMMs. SIKS Mut BMMs are SIK3+/− cells that are also depleted of SIK1 and SIK2 by RNAi-mediated knockdown. Immunoblot showing phospho-HDAC4 as well as phospho-CRTC2 protein amounts in SIKs Mut cells. Amounts of acetylated and total p65 indicated. ChIP assay of BMMs showing HDAC4 (FIG. 8C) and p65 recruitment (FIG. 8D) to TNFα and IL12β promoters in WT or SIKs Mut BMMs. Cytokine mRNA amounts (FIG. 8E) and protein secretion (FIG. 8F) from WT or SIKs Mut BMMs exposed to LPS and PGE2.

DESCRIPTION OF ILLUSTRATIVE EMBODIMENTS

The present invention provides, in some aspects, methods for treating a bacterial infection in a subject by administering to the subject a therapeutically effective amount of a class IIa HDAC inhibitor the subject. The bacterial infection may promote or cause increases in cAMP in the subject (e.g., by secretion of a toxin that increases cAMP in the subject), which may increase the difficulty associated with treating the bacterial infection; for example, the bacterial infection may result from or be cholera, anthrax, or tuberculosis. As shown in the below examples, cAMP can stimulate histone deacetylase HDAC4 in macrophages to reduce inflammatory gene expression.

Obesity promotes systemic insulin resistance through inflammatory changes that lead to the release of cytokines from activated macrophages. The second messenger cAMP has been found to attenuate macrophage activity in response to a variety of hormonal signals. As shown in the below examples, in the setting of acute over-nutrition, leptin triggers catecholamine-dependent increases in cAMP signaling that reduce inflammatory gene expression via the activation of the histone deacetylase HDAC4. cAMP stimulates HDAC4 activity through the PKA-dependent inhibition of the salt inducible kinases (SIKs), which otherwise phosphorylate and sequester HDAC4 in the cytoplasm. Without wishing to be bound by any theory, the data supports the idea that following its dephosphorylation, HDAC4 shuttles to the nucleus where it inhibits NFkB activity over pro-inflammatory genes. Variants in the HDAC4 gene are associated with obesity in humans, and these results indicate that the cAMP-HDAC4 pathway functions in maintaining insulin sensitivity and energy balance via its effects on the innate immune system.

I. Class IIa HDAC Inhibitors

Histone deacetylase proteins (HDACs) are a class of enzymes that remove acetyl groups (O=C—CH3) from an ε-N-acetyl lysine amino acid on a histone, allowing histones to wrap DNA more tightly. Histone deacetylase activation increases the deacetylation activity leading to transcriptional silencing.

In various aspects of the present invention, a class IIa HDAC inhibitor may be used to reduce help treat a bacterial infection in a subject. For example, the class IIa HDAC inhibitor may be used to reduce suppression of macrophages in a subject by the bacterial infection. Class IIa HDAC include HDAC4, HDAC5, HDAC7, and HDAC9. In some preferred embodiments, the class IIA HDAC inhibitor inhibits HDAC4.

In some embodiments the class IIa HDAC inhibitor is valproic acid (sodium 2-propylpentanoate). Valproic acid may produce anticancer, anti-inflammatory, and/or neuroprotective effects. Valproic acid may display anticonvulsive activity by increasing GABA levels, and valproic acid can decrease Aβ production in animal models of Alzheimer's disease (Phiel et al., 2001Qing et al., 2008). Valproic acid may also attenuate NMDA-mediated excitation, block voltage-gated Na+ channels, and modulate firing of neurons. In some embodiments, the sodium salt of valproic acid may be used:

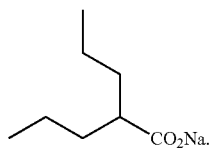

In some embodiments the class IIa HDAC inhibitor is Trichostatin A ((2E,4E,6R)-7-(4-(Dimethylamino)phenyl)-N-hydroxy-4,6-dimethyl-7-oxo-2,4-heptadienamide). Trichostatin A is a selective and potent inhibitor of histone deacetylase ($K_i$=~3.4 nM) that has been shown to be active in vivo (Yoshida et al., 1990). Trichostatin A has displayed some anticancer properties. Trichostatin A has the structure:

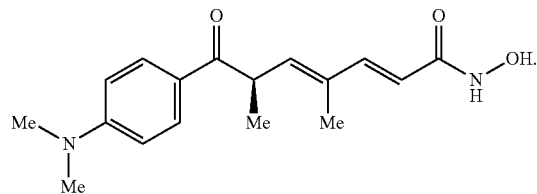 [SMILES: CC(/C=C/C(=O)NO)=C\[C@@H](C)C(=O)c1ccc(N(C)C)cc1]

Another class IIa HDAC inhibitor that may be used with the present invention is LMK235 (N-[[6-(Hydroxyamino)-6-oxohexyl]oxy]-3,5-dimethylbenzamide). LMK235 is a selective HDAC4 and HDAC5 inhibitor (e.g., $IC_{50}$ values of 4.22 and 11.9 nM have been observed for HDAC5 and HDAC4, respectively). LMK235 has shown activity against chemoresistant ovarian cancer cell lines (Marek et at (2013). LMK235 has the structure:

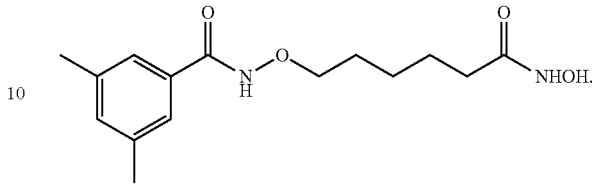

In some embodiments the class IIa HDAC inhibitor is MC1568 (3-[5-(3-(3-Fluorophenyl)-3-oxopropen-1-yl)-1-methyl-1H-pyrrol-2-yl]-N-hydroxy-2-propenamide).

MC1568 is a selective inhibitor of class IIa histone deacetylases (HDACs), and can be used to inhibit HDAC4 and HDAC5 in vivo. MC1568 may produce little or no inhibition of class I HDAC activity or expression (Mai et al., 2005; Mai et al. 2007; Nebbioso et al., 2009). MC1568 has the structure:

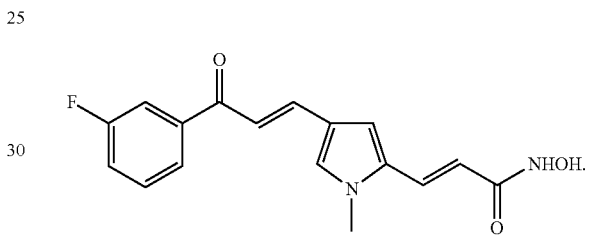

In some embodiments the class IIa HDAC inhibitor is SAHA (N-Hydroxy-N-phenyloctanediamide, also called vorinostat). SAHA can inhibit class I and II HDACs. SAHA has exhibited some antineoplastic properties (Marks and Breslow 2007). SAHA has the structure:

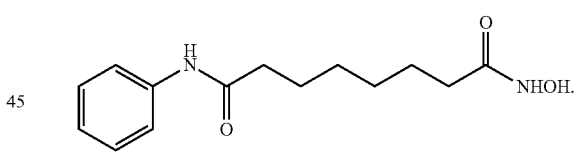

II. Combination Therapies

In some embodiments, a class IIa HDAC inhibitor (e.g., a HDAC4 selective inhibitor) may be administered in combination with a second therapy to treat a bacterial infection. The second therapy may be administered before, concurrently with, or following administration of the class IIa HDAC inhibitor (e.g., HDAC4 selective inhibitor). The class IIa HDAC inhibitor may precede or follow administration of the one or more second therapy by intervals ranging from minutes to weeks. In embodiments where the second therapy and the class IIa HDAC inhibitor are administered separately, one would generally ensure that a significant period of time did not expire between the time of each delivery, such that each agent would still be able to exert an advantageously combined effect. In such instances, it is contemplated that one would typically administer the class IIa HDAC inhibitor and the other therapeutic agent within about 12-24 hours of each other and, more preferably, within about 6-12 hours of each other, with a delay time of less than about 12 hours being most preferred. In some situations, it may be useful to extend the time period for treatment significantly, e.g., wherein several days (2, 3, 4, 5, 6 or 7) lapse between the respective administrations.

It also is conceivable that more than one administration of a class IIa HDAC inhibitor such as (e.g., a HDAC4 inhibitor) or the second therapy will be desired. In this regard, various combinations may be employed. By way of illustration, where the class IIa HDAC inhibitor is "A" and the second therapy is "B", the following permutations based on 3 and 4 total administrations are exemplary:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated. Non-limiting examples of pharmacological agents that may be used in the present invention include any pharmacological agent known to be of benefit in the treatment of a bacterial infection.

A. Anthrax

One or more antibiotics may be given in combination with a class IIa HDAC inhibitor (e.g., a HDAC4 selective inhibitor) for the treatment of anthrax (*Bacillus anthracis*) infection. The antibiotic may be a fluoroquinolone (e.g, ciprofloxacin), doxycycline, erythromycin, vancomycin, or penicillin. FDA-approved agents include ciprofloxacin, doxycycline, or penicillin. The antibiotic may be administered to the subject, e.g., orally or intravenously.

In some embodiments, the second therapy to treat anthrax may be an antibody, such as a monoclonal humanized antibody. For example, the antibody may selectively bind protective antigen (PA) component of the lethal toxin of *Bacillus anthracis*. In some embodiments, the antibody is raxibacumab. Raxibacumab is a monoclonal antibody that can selectively bind and neutralize toxins produced by *B. anthracis*.

B. Tuberculosis

One or more antibiotics may be given in combination with a class IIa HDAC inhibitor (e.g., a HDAC4 selective inhibitor) for the treatment of tuberculosis Tuberculosis is generally caused by mycobacteria such as *Mycobacterium tuberculosis*. The decision regarding which antibiotics may used to treat tuberculosis may be affected based on whether the tuberculosis infection is resistant to the antibiotic(s). For example, a combination of three to four antibiotics may be given administered repeatedly for an extended period of time (e.g., 18 to 24 months) to a subject who is infected with a multi-drug resistant tuberculosis. In some embodiments, the antibiotic is streptomycin, bedaquiline, or delamanid.

C. Pertussis

One or more antibiotics may be given in combination with a class IIa HDAC inhibitor (e.g., a HDAC4 selective inhibitor) for the treatment of pertussis (*Bordetella pertussis*). The antibiotic may be, e.g., erythromycin, azithromycin, or Trimethoprim-sulfamethoxazole (TMP-SMZ).

II. Pharmaceutical Preparations

The class IIa HDAC inhibitor (e.g., a HDAC4 selective inhibitor) may be administered to a subject, e.g., a mammalian subject such as a human patient, in a variety of pharmaceutical preparations for the treatment of a bacterial infection. In some embodiments, the class IIa HDAC inhibitor or HDAC4 selective inhibitor is formulated for oral, intravenous, or parenteral administration. In some embodiments, the pharmaceutical preparation comprises a second anti-bacterial agent such as, e.g., an antibiotic as mentioned above.

Pharmaceutical compositions of the present invention comprise an effective amount of one or more compounds of the present invention, e.g., a class IIa HDAC inhibitor, or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound or class IIa HDAC inhibitor or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., additional antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compound or class IIa HDAC inhibitor of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, via inhalation (e.g., aerosol inhalation), via intracranial administration or administration to the central nervous system, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound or class IIa HDAC inhibitor of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound or class IIa HDAC inhibitor of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound or class IIa HDAC inhibitor of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In preferred embodiments of the present invention, a compound or class IIa HDAC inhibitor of the present invention are formulated to be administered via an alimentary route. Alimentary routes include all possible routes of administration in which the composition is in direct contact with the alimentary tract. For example, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In some embodiments, a class IIa HDAC inhibitor of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Experimental Procedures

Cells:

Bone marrow macrophage cells (BMMs) were prepared from mouse bone marrow cells as described (Weischenfeldt and Porse, 2008).

Mice:

C57BL/6J, ob/ob, LysMcre and I110 Knockout (KO) mice were purchased from The Jackson Laboratory. CRTC2 and CRTC3 KO mice were described previously (Song et al., 2010; Wang et al., 2010). In studies with LKB1 KO macrophages, BMMs from floxed LKB1 mice (Bardeesy et al., 2002) were infected with cre-expressing or control GAL4-expressing lentivirus. HDAC4 fl/fl mice have been described (Vega et al., 2004). SIK3 KO mice (Uebi et al., 2012) were kindly provided by Hiroshi Takemori (Osaka). Floxed HDAC4 mice (Potthoff et al., 2007) were provided by Eric Olson (UTSW). Macrophage specific knockout of HDAC4 was obtained by a two-step cross of HDAC4 fl/fl mice with LysMcre mice.

Cytokine and Metabolite Analysis: Mice were injected with LPS (30 mg/kg) with or without Rolipram (5 mg/kg for 16 hours (h) and serum was obtained through cardiac puncture. BMMs were stimulated with LPS (10 ng/ml) with or without PGE2 (100 nM) for 16 hr and supernatant was collected.

All mice were housed in colony cages with a 12 hr light/dark cycle in a temperature-controlled environment. For LPS-induced sepsis, mice were injected intraperitoneally with 30 mg/kg LPS or PBS (UT). Survival after LPS was monitored. For studies with KO mice, age-matched wild-type littermates were employed as controls.

For HFD studies, 6-week-old mice were transferred to a 60% HFD (Research Diets, D12492) for 4 to 12 weeks as indicated. Magnetic resonance imaging scans for fat and lean mass were performed using an Echo MRI-100 instrument according to the manufacturer's instructions. For metabolic cage studies, mice were individually housed for at least 2 days. Food intake, total activity, oxygen consumption and carbon dioxide production were simultaneously measured for individually housed mice with a LabMaster system (TSE Systems). Data were collected for 2-3 days and analyzed.

GTT, ITT:

For glucose tolerance testing, mice were fasted for 16 h and then injected i.p. with glucose (1.5 g/kg). For insulin tolerance testing, mice were fasted 2 h and injected i.p. with insulin (Humulin; 1 U/kg). Rolipram (5 mg/kg/day) was injected i.p. for 7 days. Blood was collected from the tail vein and glucose levels were measured with a One Touch Ultra Glucometer (Johnson & Johnson).

Histology:

Tissues were fixed and paraffin embedded. Sections (5 μm) were used for haematoxylin and eosin staining or immunohistochemistry. For studies with adipose tissue macrophages, rehydrated antigen retrieved sections were incubated with F4/80 (Abcam) antiserum and visualized by the avidin-biotin-complex method using diaminobenzidine (Vector Labs).

Chromatin Immunoprecipitation (ChIP):

BMMs were plated in 150-mm plates and exposed to LPS (10 ng/ml) with or without PGE2 (100 nM) for 1 hr. ChIP assays were performed as described (Screaton et al., 2004). RNA was isolated by RNeasy kit (Qiagen). Primer sequences are shown in Table S3.

Blotting and Immunostaining:

Immunoblot, immunoprecipitation, and immunostaining assays were performed as described (Altarejos et al., 2008). Anti-CRTC2 antibodies were described previously (Koo et al., 2005).

Luciferase Reporter Assay:

HEK293T cells were transfected with NFκB-Luc reporter, RSV-βgal, and indicated plasmids for 48 h and luciferase assays were performed (Liu et al., 2008).

Statistical Analyses:

All studies were performed on at least three independent occasions. Results are reported as mean±s.e.m. The comparison of different groups was carried out using two-tailed unpaired Student's t-test or two-way Anova test. Differences were considered statistically significant at $*P<0.05$ and $**P<0.01$.

RT-PCR Primers are listed below in Table 1.

TABLE 1

| RT-PCR Primers | | |
|---|---|---|
| tnfa 5 | TGAACTTCGGGGTGATCGGTC | (SEQ ID NO: 1) |
| tnfa 3 | AGCCTTGTCCCTTGAAGAGGAC | (SEQ ID NO: 2) |
| il12b 5 | GTAGAGGTGGACTGGACTCC | (SEQ ID NO: 3) |
| il12b 3 | GCAGACAGAGACGCCATTCC | (SEQ ID NO: 4) |
| il10 5 | GGACAACATACTGCTAACCG | (SEQ ID NO: 5) |
| il10 3 | TTCATGGCCTTGTAGACACC | (SEQ ID NO: 6) |
| ifnb 5 | TCCAAGAAAGGACGAACATTCG | (SEQ ID NO: 7) |
| ifnb 3 | TGAGGACATCTCCCACGTCAA | (SEQ ID NO: 8) |
| HDAC4 5 | CTGCAAGTGGCCCCTACAG | (SEQ ID NO: 9) |
| HDAC4 3 | CTGCTCATGTTGACGCTGGA | (SEQ ID NO: 10) |
| HDAC5 5 | TGCAGCACGTTTTGCTCCT | (SEQ ID NO: 11) |
| HDAC5 3 | GACAGCTCCCCAGTTTTGGT | (SEQ ID NO: 12) |
| HDAC7 5 | GGCAGGCTTACACCAGCAA | (SEQ ID NO: 13) |
| HDAC7 3 | TGGGCAGGCTGTAGGGAATA | (SEQ ID NO: 14) |
| CCl3 5 | TTCTCTGTACCATGACACTCTGC | (SEQ ID NO: 15) |
| CCl3 3 | CGTGGAATCTTCCGGCTGTAG | (SEQ ID NO: 16) |
| F4/80 5 | TGACTCACCTTGTGGTCCTAA | (SEQ ID NO: 17) |

TABLE 1-continued

RT-PCR Primers

| F4/80 3 | CTTCCCAGAATCCAGTCTTTCC | (SEQ ID NO: 18) |
|---|---|---|
| CD11b 5 | ATGGACGCTGATGGCAATACC | (SEQ ID NO: 19) |
| CD11b 3 | TCCCCATTCACGTCTCCCA | (SEQ ID NO: 20) |
| tlr7 5 | ATGTGGACACGGAAGAGACAA | (SEQ ID NO: 21) |
| tlr7 3 | GGTAAGGGTAAGATTGGTGGTG | (SEQ ID NO: 22) |
| actin 5 | AACATCGAAGAGGACTTCCGA | (SEQ ID NO: 23) |
| actin 3 | CAAGCGTTCACCTGAGATGAC | (SEQ ID NO: 24) |
| FASN 5 | GGAGGTGGTGATAGCCGGTAT | (SEQ ID NO: 25) |
| FASN 3 | TGGGTAATCCATAGAGCCCAG | (SEQ ID NO: 26) |
| ACC1 5 | GATGAACCATCTCCGTTGGC | (SEQ ID NO: 27) |
| ACC1 3 | GACCCAATTATGAATCGGGAGTG | (SEQ ID NO: 28) |
| SCD1 5 | TTCTTGCGATACACTCTGGTGC | (SEQ ID NO: 29) |
| SCD1 3 | CGGGATTGAATGTTCTTGTCGT | (SEQ ID NO: 30) |

TABLE 2

ChIP Primers

| il12 chip 5 | AGTATCTCTGCCTCCTTCCTT | (SEQ ID NO: 31) |
|---|---|---|
| il12 chip 3 | GCAACACTGAAAACTAGTGTC | (SEQ ID NO: 32) |
| tnfa chip 5 | CCCCAGATTGCCACAGAATC | (SEQ ID NO: 33) |
| tnfa chip 3 | CCAGTGAGTGAAAGGGACAG | (SEQ ID NO: 34) |

Cytokine and Metabolite Analysis:

Serum or supernatant TNFα, IL-12b, and IL-10 concentrations were determined by ELISA kits from eBioscience according to manufacturer's instructions. Serum insulin (CRYSTAL CHEM INC.), leptin (Millipore), Triglyceride (Biovision), free fatty acid (Biovision), cAMP (Cayman), and noradrenaline (Thermo Fisher) levels were determined by ELISA. ChIP and Q-PCR Analysis: Primer sequences are shown in supplemental table 3. Mouse tnfα ChIP sequence covers NF kB binding site from −650 to −460. Mouse il12b ChIP sequence covers NFkB binding site from −210 to −40. Mouse 36b4 intron 3 non-targeting sequence was used as a negative control.

Human Subjects:

Genetic association studies were undertaken in subjects from the Multi-Ethnic Study of Atherosclerosis (MESA). A detailed description of the MESA study design and methods has been published previously (Bild et al., 2002). Briefly, 6,814 participants 45 to 84 years of age who identified themselves as white (2,748), black (1,930), Hispanic/Latino (1,496), or Chinese (806) were recruited from six US communities between 2000 and 2002.

Genotyping of human samples: We utilized genome wide association (GWAS) data previously generated in MESA, including imputed genotypes. GWAS and the phenotypes of interest were available for 2268 whites, 1288 blacks, 1116 Hispanics, and 606 Chinese subjects. GWAS data was searched for SNPs in and around (100 kb upstream and 100 kb downstream) HDAC4, HDAC5, and HDAC7A, for assessment of their association with adiposity traits, which consisted of 499 single nucleotide polymorphisms (SNPs) in HDAC4, 109 SNPs in HDAC5, and 235 SNPs in HDAC7A.

Human Genetic Association Analysis:

We used PLINK (Purcell et al., 2007) to test hypothesized associations between SNPs in the HDAC genes and BMI and waist circumference. We first conducted a discovery effort in the MESA white subjects. Positive associations with adiposity traits were followed up in the remaining three ethnic groups (black, Chinese, Hispanic). BMI was log transformed to better approximate conditional normality and homogeneity of variance. An additive genetic model was assumed. Analyses were conducted using age, sex, study site and principal components as covariates.

Antibodies, and Reagents:

LPS, 8-Bromoadenosine 3,5'-cyclic monophosphate sodium salt (8-Br-cAMP), Prostaglandin E2 (PGE2), Isoprenaline hydrochloride(Iso), rolipram, pertussis toxin and cholera toxin were purchased from Sigma. Anthrax edema factor (EF) and protective antigen (PA) were purchased from List Biological Labs Inc. Anti-p65, anti-phospho (Ser536) p65, anti-HDAC4, anti-phospho (Ser246) HDAC4, anti-phospho (Thr246/Tyr185) JNK, anti-phospho (Thr180/Tyr182) P38, anti-phospho (Ser32/36) IκBα, antiacetyl Histone H4 Lys5, anti-Histone H4 and anti-CRTC3 antibodies were purchased from Cell Signaling Technology. Anti-LKB1 antibody was purchased from Santa Cruz Biotechnology. Anti-acetyl p65 Lys310 and anti-F4/80 were purchased from Abcam.

Example 2

Leptin-Mediated Increases in Catecholamine Signaling Reduce Adipose Tissue Inflammation Via Activation of Macrophage HDAC4

Acute effects of cAMP on the inflammatory response to bacterial lipopolysaccharide (LPS) were tested. Administration of LPS (30 mg/kg) into adult C57BL/6J mice increased circulating concentrations of the pro-inflammatory cytokines (TNFα, IL1213) and promoted lethality within 1-2 days (FIGS. 1A-B and FIG. 5A). Co-administration of the phospho-diesterase 4 (PDE4) inhibitor Rolipram (5 mg/kg) blocked effects of LPS on cytokine release and survival (FIGS. 1A-F and FIGS. 5A-C) (Herve et al., 2008). Moreover, exposure of cultured bone marrow macrophages (BMMs) to prostaglandin E2 (PGE2), a paracrine hormone that stimulates cAMP production (Okonogi et al., 1991), reduced pro-inflammatory cytokine mRNA amounts and secretion from cultured cells exposed to LPS (FIGS. 1C-D and FIG. 5B). We observed similar effects using the β2 adrenergic receptor agonist isoproterenol or the cell permeable cAMP analog 8-Br-cAMP. In keeping with their stimulatory effects on the cAMP pathway, exposure of BMMs to bacterial toxins such as pertussis toxin, cholera toxin, or edema factor also lowered cytokine gene expression (FIG. 5C).

The TLR signaling pathway has been shown to stimulate a signaling cascade that culminates in the activation of NF-κB (Hayden and Ghosh, 2008; Takeda and Akira, 2004). Exposure to PGE2 did not interfere with the activation of P38 or JNK, or with the phosphorylation of either IκBα or the NF-κB subunit p65 in response to LPS (FIG. 1E); but it blocked LPS-dependent increases in both p65 and histone H4K5 acetylation over cytokine promoters (FIGS. 1E-F). Consequently, p65 recruitment to the TNFα and IL12β promoters was reduced in cells co-treated with LPS plus PGE2 compared to LPS alone.

Role of the CREB/CRTC Pathway in Macrophages

Based on the ability for the CREB/CRTC pathway to stimulate the expression of the anti-inflammatory cytokine IL10 in macrophages (Clark et al., 2012; MacKenzie et al., 2013), the inventors considered whether cAMP signals inhibit pro-inflammatory cytokine production via this mechanism. CRTC2 and CRTC3 were readily detected in cultured BMMs; they were confined to the cytoplasm under basal conditions and following exposure to LPS (FIGS. 6A-B). Co-treatment of LPS with PGE2 agonist triggered CRTC2/3 dephosphorylation and nuclear translocation. As a result, IL10 mRNA and protein secretion were upregulated in wild-type cells exposed to LPS plus PGE2 but less so in BMMs from CRTC2 knockout (KO) or CRTC3 KO mice (FIGS. 6C-D). In keeping with the reduction in IL10, TNFα and IL12β mRNA amounts were increased in CRTC2 and CRTC3 KO BMMs; we observed similar differences in IL10 KO cells (FIGS. 6F-G). Despite these changes, PGE2 was still effective in blocking p65 promoter recruitment and in down-regulating TNFα and IL12β production in CRTC2 KO and CRTC3 KO cells (FIGS. 6C-E). Taken together, these results suggest that the CREB/CRTC pathway exerts an anti-inflammatory role in BMMs via its effects on IL10, but that a second pathway also mediates effects of cAMP on NF-κB activity.

Class IIa HDACs Mediate Effects of cAMP

Having seen that exposure to cAMP promotes the deacetylation of p65 and histone H4K5, we evaluated the potential role of the cAMP/class IIa HDAC pathway in this setting. Of the three family members (HDAC 4, 5, 7), HDAC4 is the most highly expressed in macrophages (FIG. 7A). Similar to the CRTCs, HDAC4 is phosphorylated at consensus SIK recognition sites and sequestered in the cytoplasm under basal conditions and following stimulation with LPS (FIGS. 2A-B). Exposure of wild-type BMMs to PGE2 in combination with LPS triggered HDAC4 dephosphorylation at Ser246 and nuclear translocation. As a result, HDAC4 recruitment to the TNFα and IL12β promoters increased in cells treated with PGE2+LPS compared to LPS alone (FIG. 2C). Based on these effects, we tested whether HDAC4 associates with p65. Supporting this idea, we recovered endogenous p65 from IPs of endogenous HDAC4 that were prepared from BMMs exposed to LPS and PGE2 but not LPS alone (FIG. 7C). We obtained similar results in co-IP studies using epitope-tagged p65 and HDAC4 expression vectors. Consistent with this association, over-expression of wild-type and to a greater extent phosphorylation-defective HDAC4 or HDAC5 decreased NF-κB reporter activity in cells co-expressing p65 (FIG. 7B).

To further evaluate the role of HDAC4 in modulating cytokine gene expression, BMMs from mice with a macrophage specific knockout of HDAC4 (HDAC4 MKO) were used. Exposure of wild-type or HDAC4 MKO BMMs to LPS alone increased the acetylation and recruitment of p65 to cytokine promoters comparably (FIGS. 2A, D). By contrast with the inhibitory effects of PGE2 in control BMMs, however, exposure to PGE2 did not reduce amounts of acetylated p65 or down regulate p65 recruitment; and it did not diminish histone H4K5 acetylation over TNFα and IL12β promoters in HDAC4 MKO cells (FIGS. 2A, D, E). Consequently, TNFα and IL12β mRNA and protein secretion were nearly fully rescued in HDAC4 MKO BMMs co-stimulated with LPS and PGE2 relative to LPS alone (FIGS. 7D, E).

We examined effects of HDAC4 MKO on the inflammatory response in vivo. LPS administration increased circulating concentrations of TNFα and IL12β and promoted lethality comparably in wild-type and HDAC4 MKO mice (FIG. 2F). Although rolipram co-administration improved survival in LPS-treated control mice, it had modest effects in HDAC4 MKO littermates. These results demonstrate that HDAC4 associates with and inhibits NF-κB activity in response to cAMP.

Role of SIKs in Regulating Class IIa HDACs cAMP has been shown to promote the dephosphorylation and nuclear shuttling of Class IIa HDACs through PKA-mediated inhibition of the SIKs (Berdeaux et al., 2007; Mihaylova et al., 2011; Wang et al., 2011). Based on the importance of the master kinase LKB1 in activating SIKs, we evaluated effects of LKB1 gene disruption on HDAC4 activity. Knockout of LKB1 in BMMs led to HDAC4 dephosphorylation and nuclear translocation (FIGS. 3A-B). Indeed, HDAC4 occupancy over the TNFα and IL12β promoters was constitutively elevated in LKB1 mutant cells (FIG. 3C). As a consequence, p65 acetylation and promoter recruitment were reduced in LKB1 KO BMMs, leading to decreases in cytokine production (FIGS. 3A-F). Indeed, reducing SIK activity, with a small molecule inhibitor (staurosporine), or by RNAi-mediated knockdown of SIK expression, decreased cytokine gene expression in BMMs exposed to LPS (FIGS. 8A-F). These results support the idea that cAMP modulates cytokine gene expression through inactivation of the LKB1/SIK pathway and consequent induction of class IIa HDACs.

Role of HDAC4 in Obesity

Over-nutrition triggers leptin-mediated increases in sympathetic nerve activity that stimulate the mobilization of triglycerides from adipose. Leptin injection into ob/ob mice upregulated circulating concentrations of norepinephrine as well as cAMP content in epididymal fat pads (FIG. 4A). The rise in cAMP appeared to be catecholamine dependent, because it was blocked by administration of β adrenergic antagonist. In keeping with these effects, leptin administration also promoted HDAC4 de-phosphorylation in WAT; these effects were propranolol-sensitive (FIG. 7H). As a result, leptin stimulated the nuclear translocation of HDAC4 in adipose resident macrophages (FIG. 4B).

Short term HFD feeding (4 weeks) also triggered increases in circulating norepinephrine that stimulated the cAMP-HDAC4 pathway in adipose tissue macrophages (FIGS. 7A-F). But long-term (12 weeks) HFD feeding had more modest effects on HDAC4 dephosphorylation, reflecting increases in leptin resistance that attenuate sympathetic nerve activity in WAT.

Obesity has been shown to promote insulin resistance through increases in macrophage infiltration into white adipose tissue and liver (Arkan et al., 2005; Hotamisligil, 2006). Based on its inhibitory effects on NF-κB activity, the inventors wondered whether the cAMP-HDAC4 pathway protects against insulin resistance. To test this notion, we evaluated effects of HFD feeding in HDAC4 MKO versus wild-type littermates. Although they were similar to controls on normal chow, HDAC4 MKO mice had higher circulating glucose and free fatty acid concentrations after 8 weeks on a HFD (FIG. 4C). Insulin levels were also elevated in HDAC4 MKO mice; they became glucose intolerant and had reduced glucose clearance (FIG. 4D). Consistent with these profiles, macrophage infiltrates in WAT and triglyceride accumulation in liver were more pronounced in HFD-fed HDAC4 MKO versus control mice (FIG. 4E and FIGS. 7A-F).

Whether induction of the cAMP pathway improves insulin sensitivity via an HDAC4-dependent mechanism was tested. Rolipram administration for 7 days improved glucose tolerance and insulin sensitivity in wild-type but not HDAC4 MKO littermates under HFD conditions (FIG. 4F). These results demonstrate that HDAC4 acts downstream of cAMP in macrophages.

Superimposed on these metabolic changes, HDAC4 MKO mice gained more weight on a HFD, and they had increased adiposity (FIGS. 4G-H). Indeed, HDAC4 MKO mice had increased food intake with decreased oxygen consumption as well as physical activity (FIGS. 7J-K). Realizing that these increases in body weight could contribute to inflammatory changes in HDAC4 MKO mice, these animals were evaluated after 4 weeks of HFD feeding, when body weights and adiposity in HDAC4 mutants are comparable to controls (FIG. 7L). Consistent with their increases in adipose tissue macrophages, HDAC4 MKO mice were more glucose intolerant and insulin resistant by GTT and ITT testing.

Based on the effects of HDAC4 in mice, the inventors tested whether a similar role for class IIa HDACs may exist in humans, via a two-stage genetic association study of the HDAC4 (chromosome 2q37.3), HDAC5 (chromosome 17q21), and HDAC7A (chromosome 12q13.1) genes, conducted in the Multi-Ethnic Study of Atherosclerosis (MESA). In the first stage, we assessed association of variants in these three genes with body mass index and waist circumference in 2268 white subjects. Seventy HDAC4 SNPs were associated with BMI and 44 HDAC4 SNPs were associated with waist circumference; 30 of these SNPs were associated with both traits. The number of associations with BMI was well in excess of the number expected by chance (70 versus 25, $\chi^2=19.5$, P<0.0001) as was the number of SNPs associated with waist circumference (44 versus 25, $\chi^2=4.9$, P=0.027). On the other hand, only a few ($\leq 5$) HDAC5 SNPs and no HDAC7A SNPs were associated with these traits. In the second stage (Table 3 and Table 4), we found that a significant fraction of HDAC4 SNPs associated with BMI and waist circumference in whites were also associated with these traits in black and Chinese subjects. Most of these associations had the same direction of effect as those observed in whites. Remarkably, seven SNPs replicated in blacks were associated with both BMI and waist circumference; these SNPs were concentrated in the proximal end of the gene, particularly in intron 2, suggesting that this region of the gene harbors a functional variant that influences obesity in whites and blacks.

Our results demonstrate that increases in sympathetic nerve activity in response to acute over-nutrition trigger the activation of two cAMP-responsive pathways-the CRTCs and class IIa HDACs. Both pathways inhibit the production of inflammatory mediators via induction of IL10 and repression of NF-κB, respectively. As IL10 has also been found to promote insulin sensitivity in the setting of diet-induced obesity (Hong et al., 2009), we imagine that the CRTC pathway may have salutary effects in this context. During the preparation of this manuscript, Abu-Farha et al reported that HDAC4 expression is down-regulated in adipose from obese subjects (Abu-Farha et al., 2013). Our results extend these studies by showing that disruption of HDAC4 in macrophages is sufficient to promote insulin resistance and obesity.

In addition to HDAC4, a number of regulatory factors including SirT1 (Schug et al., 2010) and KLF4 (Liao et al., 2011) have been shown to modulate energy balance through their effects in macrophages. Alternatively activated M2 macrophages can modulate energy expenditure by secreting catecholamines and enhancing brown fat thermogenesis, for example (Nguyen et al., 2011). Without wishing to be bound by any theory, it is conceived that HDAC4 and other regulators may modulate energy expenditure through effects on a secreted factor.

The first stage of the human genetic association study found association of several HDAC4 SNPs with BMI and waist circumference in 2268 white subjects. In the second stage, we examined the significant HDAC4 SNPs for association with BMI and waist circumference in the remaining MESA ethnic groups. Of the 70 SNPs associated with BMI in whites, 14 were associated with BMI in black subjects, 17 were associated with BMI in the Chinese, and none were associated with BMI in the Hispanics (Table 3). Most of these associations (11 SNPs in blacks, 13 SNPs in Chinese) had the same direction of effect in these ethnic groups as observed in the whites, and are indicated as "replicated" SNPs in Table 3. Of the 44 SNPs associated with waist circumference in whites, 9 were associated with waist circumference in the black subjects, with effects in the same direction as observed in the whites (replicated SNPs) (Table 4). Seven SNPs replicated in blacks were associated with both BMI and waist circumference; these SNPs were concentrated in the proximal end of the gene, particularly intron 2, suggesting that this region of the gene harbors a functional variant that influences obesity in whites and blacks. We examined these seven SNPs in RegulomeDB, a database that annotates non-coding SNPs with known and predicted regulatory DNA elements including transcription factor binding sites, DNAse hypersensitivity, biochemically characterized promoter elements, and expression quantitative trait loci (Boyle et al., 2012). Based on transcription factor binding, alteration of binding motifs, and DNase hypersensitivity, one of the SNPs, rs6705378, was found to have a high likelihood of functionality (RegulomeDB score of 2b). Future experimentation will be required to assess the effect of this SNP on HDAC4 expression.

TABLE 3

SNPs associated with BMI in whites that were also associated with BMI in other ethnic groups

| SNP | Position (37.1) | Location | Coded allele | P value (white) | beta (white) | P value (black) | beta (black) | P value (Chinese) | beta (Chinese) | P value (Hispanic) | beta (Hispanic) | Replicated BMI SNP |
|---|---|---|---|---|---|---|---|---|---|---|---|---|
| rs3791423 | 240,038,687 | intron 11 | G | 0.038 | −0.020 | 0.016 | −0.054 | 0.787 | 0.004 | 0.975 | 0.0003 | white-black |
| rs4572614 | 240,054,206 | intron 10 | G | 0.011 | 0.018 | 0.019 | −0.018 | 0.512 | −0.012 | 0.464 | −0.006 | |
| rs3791471 | 240,059,625 | intron 9 | T | 0.020 | −0.016 | 0.018 | 0.019 | 0.408 | 0.016 | 0.455 | 0.006 | |
| rs3791473 | 240,059,733 | intron 9 | G | 0.011 | 0.018 | 0.033 | −0.017 | 0.438 | −0.015 | 0.385 | −0.007 | |
| rs2290087 | 240,066,417 | intron 7 | G | 0.030 | −0.016 | 0.023 | −0.045 | 0.093 | −0.019 | 0.890 | −0.001 | white-black |
| rs2100171 | 240,069,503 | intron 7 | C | 0.029 | 0.016 | 0.027 | 0.045 | 0.091 | 0.019 | 0.855 | 0.001 | white-black |
| rs3791520 | 240,087,644 | intron 5 | G | 0.050 | −0.015 | 0.013 | −0.026 | 0.037 | −0.024 | 0.934 | −0.001 | white-black-Chinese |
| rs2411424 | 240,092,430 | intron 5 | G | 0.049 | −0.015 | 0.089 | −0.019 | 0.036 | −0.024 | 0.957 | 0.0004 | white-Chinese |

TABLE 3-continued

SNPs associated with BMI in whites that were also associated with BMI in other ethnic groups

| SNP | Position (37.1) | Location | Coded allele | P value (white) | beta (white) | P value (black) | beta (black) | P value (Chinese) | beta (Chinese) | P value (Hispanic) | beta (Hispanic) | Replicated BMI SNP |
|---|---|---|---|---|---|---|---|---|---|---|---|---|
| rs3791529 | 240,092,523 | intron 5 | G | 0.012 | 0.015 | 0.259 | 0.011 | 0.028 | 0.018 | 0.490 | −0.005 | white-Chinese |
| rs688606 | 240,101,095 | intron 4 | T | 0.029 | 0.019 | 0.309 | 0.025 | 0.041 | 0.061 | 0.700 | 0.006 | white-Chinese |
| rs551326 | 240,101,611 | intron 4 | T | 0.043 | 0.015 | 0.194 | 0.011 | 0.044 | 0.021 | 0.764 | −0.002 | white-Chinese |
| rs506324 | 240,104,346 | intron 4 | T | 0.020 | 0.014 | 0.654 | 0.004 | 0.030 | 0.017 | 0.686 | −0.003 | white-Chinese |
| rs681715 | 240,104,389 | intron 4 | T | 0.019 | 0.014 | 0.605 | 0.004 | 0.017 | 0.019 | 0.630 | −0.003 | white-Chinese |
| rs291332 | 240,145,305 | intron 3 | T | 0.029 | 0.017 | 0.593 | 0.007 | 0.015 | 0.081 | 0.235 | 0.013 | white-Chinese |
| rs291336 | 240,148,039 | intron 3 | T | 0.012 | 0.021 | 0.720 | 0.008 | 0.008 | 0.116 | 0.255 | 0.015 | white-Chinese |
| rs291338 | 240,149,962 | intron 3 | G | 0.027 | −0.017 | 0.552 | −0.008 | 0.013 | −0.085 | 0.234 | −0.013 | white-Chinese |
| rs496316 | 240,155,231 | intron 3 | T | 0.014 | −0.018 | 0.531 | −0.008 | 0.026 | −0.072 | 0.107 | −0.017 | white-Chinese |
| rs12151594 | 240,174,796 | intron 2 | T | 0.017 | −0.017 | 0.107 | 0.016 | 0.016 | −0.082 | 0.172 | −0.014 | white-Chinese |
| rs12151462 | 240,175,040 | intron 2 | T | 0.017 | 0.017 | 0.800 | 0.003 | 0.015 | 0.083 | 0.065 | 0.020 | white-Chinese |
| rs13408972 | 240,185,806 | intron 2 | G | 0.046 | 0.014 | 0.962 | 0.0005 | 0.017 | −0.056 | 0.327 | −0.011 | |
| rs6705378 | 240,193,889 | intron 2 | G | 0.033 | −0.011 | 0.013 | −0.018 | 0.234 | 0.009 | 0.085 | 0.011 | white-black* |
| rs6732673 | 240,199,204 | intron 2 | T | 0.046 | 0.011 | 0.007 | 0.020 | 0.499 | −0.005 | 0.070 | −0.012 | white-black* |
| rs13411439 | 240,201,641 | intron 2 | G | 0.016 | −0.015 | 0.036 | −0.016 | 0.024 | 0.063 | 0.510 | 0.006 | white-black* |
| rs6739632 | 240,207,019 | intron 2 | G | 0.039 | −0.014 | 0.033 | −0.016 | 0.241 | 0.015 | 0.162 | 0.012 | white-black* |
| rs6737742 | 240,216,021 | intron 2 | G | 0.043 | 0.014 | 0.014 | 0.024 | 0.089 | −0.047 | 0.200 | −0.015 | white-black* |
| rs908262 | 240,217,522 | intron 2 | C | 0.022 | 0.014 | 0.014 | 0.021 | 0.010 | −0.078 | 0.111 | −0.016 | white-black* |
| rs11686104 | 240,286,146 | intron 1 | G | 0.047 | 0.012 | 0.037 | 0.018 | 0.012 | −0.072 | 0.089 | −0.017 | white-black* |

Significant P values are indicated in bold. Replicated indicates ethnic groups in which the SNP was significant and had consistent beta values.
*SNP that also replicated association with waist circumference in whites and blacks

TABLE 4

SNPs associated with waist in whites that were also associated with waist in other ethnic groups

| SNP | Position | Location | Coded allele | P value (white) | beta (white) | P value (black) | beta (black) | P value (Chinese) | beta (Chinese) | P value (Hispanic) | beta (Hispanic) | Replicated Waist SNP |
|---|---|---|---|---|---|---|---|---|---|---|---|---|
| rs13408972 | 240,185,806 | intron 2 | G | 0.011 | 1.403 | 0.769 | −0.227 | 0.004 | −4.737 | 0.809 | 0.216 | |
| rs8705378 | 240,193,889 | intron 2 | G | 0.007 | −1.106 | 0.011 | −1.484 | 0.231 | 0.662 | 0.225 | 0.611 | white-black* |
| rs6732673 | 240,199,204 | intron 2 | T | 0.006 | 1.137 | 0.005 | 1.630 | 0.441 | −0.426 | 0.212 | −0.630 | white-black* |
| rs13411439 | 240,201,641 | intron 2 | G | 0.001 | −1.643 | 0.030 | −1.257 | 0.002 | 6.357 | 0.673 | −0.304 | white-black* |
| rs6739632 | 240,207,019 | intron 2 | G | 0.004 | −1.510 | 0.024 | −1.341 | 0.211 | 1.163 | 0.918 | 0.071 | white-black* |
| rs6737742 | 240,216,021 | intron 2 | G | 0.004 | 1.627 | 0.016 | 1.830 | 0.003 | −6.275 | 0.631 | −0.462 | white-black* |
| rs11883623 | 240,217,116 | intron 2 | T | 0.034 | 0.912 | 0.001 | 2.050 | 0.769 | −0.171 | 0.457 | 0.409 | white-black |
| rs908262 | 240,217,522 | intron 2 | C | 0.001 | 1.609 | 0.004 | 1.875 | 0.0001 | −8.601 | 0.373 | −0.705 | white-black* |
| rs8543522 | 240,228,230 | intron 2 | T | 0.008 | 1.091 | 0.039 | 1.215 | 0.728 | 0.289 | 0.808 | 0.132 | white-black |
| rs925738 | 240,241,255 | intron 2 | T | 0.042 | −0.826 | 0.585 | −0.371 | 0.003 | 3.731 | 0.415 | −0.492 | |
| rs11686104 | 240,286,146 | intron 1 | G | 0.006 | 1.337 | 0.017 | 1.642 | 0.0003 | −7.376 | 0.226 | −0.966 | white-black* |

Significant P values are indicated in bold. Replicated indicates ethnic groups in which the SNP was significant and had consistent beta values.
*SNP that also replicated association with BMI in whites and blacks Mutations in the HDAC4 gene that result in haploinsufficiency have been associated with obesity in humans, although the underlying mechanism remains unclear (Williams et al., 2010). We also found that common, non-coding variations in HDAC4 were associated with adiposity phenotypes in multiple ethnic groups (white, black, Chinese), suggesting the possibility of a wider role in physiologic regulation of obesity. Because these variants reside in introns of HDAC4, their functional role is currently unclear; they are likely to be in linkage disequilibrium with functional variants elsewhere in the gene. Of interest, no HDAC4 SNPs were associated with obesity traits in Hispanics; given that the Chinese and Hispanic sample sizes were similar, we do not believe that this was related to statistical power. We speculate that it reflects a different genetic architecture of obesity in Hispanics; we recently found such a phenomenon in that a functional variant in the CRTC3 gene was associated with obesity traits in Hispanics, but not in whites (Song et al., 2010).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,613,308
U.S. Pat. No. 5,466,468
U.S. Pat. No. 5,543,158
U.S. Pat. No. 5,641,515
U.S. Pat. No. 5,399,363
Abu-Farha et al., Proteomics Analysis of Human Obesity Reveals the Epigenetic Factor HDAC4 as a Potential Target for Obesity. PLoS ONE 8, e75342, 2013.
Agarwal et al., Cyclic AMP intoxication of macrophages by a *Mycobacterium tuberculosis* adenylate cyclase. *Nature* 460, 98-102, 2009.
Altarejos et al., The Creb1 coactivator Crtc1 is required for energy balance and fertility. *Nat Med* 14, 1112-1117, 2008.
Altarejos, J. Y., and Montminy, M., CREB and the CRTC co-activators: sensors for hormonal and metabolic signals. *Nat Rev Mol Cell Biol* 12, 141-151, 2011.
Arkan et al., IKK-beta links inflammation to obesity-induced insulin resistance. *Nat Med* 11, 191-198, 2005.
Aronoff et al., Cutting edge: macrophage inhibition by cyclic AMP (cAMP): differential roles of protein kinase A and exchange protein directly activated by cAMP-1. *J Immunol* 174, 595-599, 2005.
Bardeesy et al., Loss of the Lkb1 tumour suppressor provokes intestinal polyposis but resistance to transformation. *Nature* 419, 162-167, 2002.
Berdeaux et al., SIK1 is a class II HDAC kinase that promotes survival of skeletal myocytes. *Nat Med* 13, 597-603, 2007.
Bild et al., Multi-ethnic study of atherosclerosis:objectives and design. *Am J Epidemiol* 156: 871-881, 2002.
Boyle et al. Annotation of functional variation in personal genomes using RegulomeDB. Genome Res. 2012; 22(9): 1790-7. Epub 2012/09/08. doi: 10.1101/gr.137323.112. PubMed PMID: 22955989; PubMed Central PMCID: PMC3431494, 2012.
Clark et al., Phosphorylation of CRTC3 by the salt-inducible kinases controls the interconversion of classically activated and regulatory macrophages. *Proc Natl Acad Sci USA* 109, 16986-16991, 2012
Hayden, M. S., and Ghosh, S., Shared principles in NF-kappaB signaling. *Cell* 132, 344-362, 2008.
Herve et al., The PDE4 inhibitor rolipram prevents NF-kappaB binding activity and proinflammatory cytokine release in human chorionic cells. *J Immunol* 181, 2196-2202, 2008.
Hong et al., Interleukin-10 prevents diet-induced insulin resistance by attenuating macrophage and cytokine response in skeletal muscle. *Diabetes* 58, 2525-2535, 2009.
Hotamisligil, G. S., Inflammation and metabolic disorders. *Nature* 444, 860-867, 2006.
Koo et al., The CREB coactivator TORC2 is a key regulator of fasting glucose metabolism. *Nature* 437, 1109-1111, 2005.
Liao et al., Kruppel-like factor 4 regulates macrophage polarization. *J Clin Invest* 121, 2736-2749, 2011.
Liu et al., A fasting inducible switch modulates gluconeogenesis via activator/coactivator exchange. *Nature* 456, 269-273, 2008.
MacKenzie et al., PGE(2) induces macrophage IL-10 production and a regulatory-like phenotype via a protein kinase A-SIK-CRTC3 pathway. *J Immunol* 190, 565-577, 2013.

Mai et al., Class II (IIa)-selective histone deacetylase inhibitors. 1. Synthesis and biological evaluation of novel (aryloxopropenyl)pyrrolyl hydroxyamides. *J Med Chem.* 48(9):3344-53, 2005.
Mai et al., Identification of two new synthetic histone deacetylase inhibitors that modulate globin gene expression in erythroid cells from healthy donors and patients with thalassemia, *Mol Pharmacol.* 72(5):1111-23, 2007.
Marek et al, Histone deacetylase (HDAC) inhibitors with a novel connecting unit linker region reveal a selectivity profile for HDAC4 and HDAC5 with improved activity against chemoresistant cancer cells. *J. Med. Chem.* 56(2): 427-36, 2013.
Marks and Breslow, Dimethyl sulfoxide to vorinostat: development of this histone deacetylase inhibitor as an anticancer drug. *Nat. Biotechnol.* 25(1):84-90, 2007.
Mihaylova et al., Class IIa histone deacetylases are hormone-activated regulators of FOXO and mammalian glucose homeostasis. *Cell* 145, 607-621, 2011.
Nebbioso et al., Selective class II HDAC inhibitors may impaor myogenesis by modulating the stability and activity of HDAC-MEF2 complexes, *EMBO J.* 10:776-782, 2009.
Nguyen et al., Alternatively activated macrophages produce catecholamines to sustain adaptive thermogenesis. *Nature* 480, 104-108, 2011.
Okonogi et al., Inhibition of prostaglandin E2-stimulated cAMP accumulation by lipopolysaccharide in murine peritoneal macrophages. *J Biol Chem* 266, 10305-10312, 1991.
Phiel et al., Histone deacetylase is a direct target of valproic acid, a potent anticonvulsant, mood stabilizer, and teratogen. *J Biol Chem.* 276(39):36734-41, 2001.
Potthoff et al., Histone deacetylase degradation and MEF2 activation promote the formation of slow-twitch myofibers. *J Clin Invest* 117, 2459-2467, 2007.
Purcell et al., PLINK: a tool set for whole-genome association and population-based linkage analyses. *Am J Hum Genet* 81: 559-575, 2007.
Qing et al., Valproic acid inhibits Aβ production, neuritic plaque formation, and behavioural defects in Alzheimer's disease mouse models. *J Exp Med.* 205(12):2781-9, 2008.
Remington's Pharmaceutical Sciences, 18th Ed. Mack Printing Company, pp. 1289-1329, 1990.
Remington: The Science and Practice of Pharmacy, $21^{st}$ Ed. Lippincott Williams and Wilkins, 2005.
Schug et al., Myeloid deletion of SIRT1 induces inflammatory signaling in response to environmental stress. *Mol Cell Biol* 30, 4712-4721, 2010.
Screaton et al., The CREB coactivator TORC2 functions as a calcium- and cAMP-sensitive coincidence detector. *Cell* 119, 61-74, 2004.
Song et al., CRTC3 Links Catecholamine Signaling to Energy Balance. *Nature* 468, 933-939, 2010.
Takeda, K., and Akira, S., TLR signaling pathways. *Seminars in immunology* 16, 3-9, 2004.
Tang, W. J., and Guo, Q., The adenylyl cyclase activity of anthrax edema factor. *Molecular aspects of medicine* 30, 423-430, 2009.
Uebi et al., Involvement of SIK3 in glucose and lipid homeostasis in mice. PLoS ONE 7, e37803, 2012.
Vega et al., Histone deacetylase 4 controls chondrocyte hypertrophy during skeletogenesis. *Cell* 119, 555-566, 2004.
Wang et al., Targeted disruption of the CREB coactivator Crtc2 increases insulin sensitivity. *Proc Natl Acad Sci USA* 107, 3087-3092, 2010.

Wang et al., A hormone-dependent module regulating energy balance. *Cell* 145, 596-606, 2011.

Weischenfeldt, J., and Porse, B. Bone Marrow-Derived Macrophages (BMM): Isolation and Applications. CSH protocols 2008, pdb prot5080. 2008.

Williams et al., Haploinsufficiency of HDAC4 causes brachydactyly mental retardation syndrome, with brachydactyly type E, developmental delays, and behavioral problems. *Am J Hum Genet.* 87(2):219-28. Epub 2010/ 08/10. doi: 10.1016/j.ajhg.2010.07.011. PubMed PMID: 20691407; PubMed Central PMCID: PMC2917703, 2010.

Yoshida et al., Potent and specific inhibition of mammalian histone deacetylase both in vivo and in vitro by trichostatin A. J. Biol. Chem. 265:17174-9, 1990.

Yuan et al., Reversal of obesity- and diet-induced insulin resistance with salicylates or targeted disruption of Ikkbeta. Science 293, 1673-1677, 2001.

What is claimed is:

1. A method of inhibiting a bacterial toxin that increases or stimulates production of cAMP in a subject comprising administering an effective dose of a class IIa Histone deacetylase (HDAC) inhibitor to the subject, wherein the class IIa HDAC inhibitor is valproic acid (sodium 2-propylpentanoate), Trichostatin A ((2E,4E,6R)-7-(4-(Dimethylamino)phenyl)-N-hydroxy-4,6-dimethyl-7-oxo-2,4-heptadienamide), LMK235 (N-[[6-(Hydroxyamino)-6-oxohexyl]oxy]-3,5-dimethylbenzamide), MC1568 (3-[5-(3-(3-Fluorophenyl)-3-oxopropen-1-yl)-1-methyl-1H-pyrrol-2-yl]-N-hydroxy-2-propenamide) or SAHA (N-Hydroxy-N'-phenyloctanediamide); and wherein the inhibitor inhibits HDAC4.

2. The method of claim 1, wherein the bacterial toxin is secreted by or results from infection by anthrax (*Bacillus anthracis*), tuberculosis (*Mycobacterium tuberculosis*), pertussis (*Bordetella pertussis*), or cholera (*Vibrio cholerae*).

3. The method of claim 1, wherein the class IIa HDAC inhibitor is MC1568 (3-[5-(3-(3-Fluorophenyl)-3-oxopropen-1-yl)-1-methyl-1H-pyrrol-2-yl]-N-hydroxy-2-propenamide).

4. The method of claim 1, wherein the class IIa HDAC inhibitor is LMK235 (N-[[6-(Hydroxyamino)-6-oxohexyl]oxy]-3,5-dimethylbenzamide), MC1568 (3-[5-(3-(3-Fluorophenyl)-3-oxopropen-1-yl)-1-methyl-1H-pyrrol-2-yl]-N-hydroxy-2-propenamide), or Trichostatin A ((2E,4E,6R)-7-(4-(Dimethylamino)phenyl)-N-hydroxy-4,6-dimethyl-7-oxo-2,4-heptadienamide).

5. The method of claim 1, wherein the class IIa HDAC inhibitor is comprised in a pharmaceutical preparation comprising an excipient.

6. The method of claim 5, wherein the pharmaceutical preparation is formulated for oral, intravenous, or parenteral administration.

7. The method of claim 1, wherein the method further comprises administering a second antibacterial therapy to the subject, wherein second antibacterial therapy comprises administering an antibiotic to the subject.

8. The method of claim 7, wherein the antibiotic is ciprofloxacin, doxycycline, erythromycin, vancomycin, penicillin, streptomycin, bedaquiline, delamanid, erythromycin, azithromycin, or trimethoprim-sulfamethoxazole (TMP-SMZ).

9. The method of claim 1, wherein the subject is a human.

10. The method of claim 2, wherein the bacterial toxin is secreted by or results from infection by pertussis (*Bordetella pertussis*).

11. The method of claim 2, wherein the bacterial toxin is secreted by or results from infection by tuberculosis (*Mycobacterium tuberculosis*).

12. The method of claim 1, wherein the inhibitor is valproic acid (sodium 2-propylpentanoate).

13. The method of claim 1, wherein the inhibitor is SAHA (N-Hydroxy N' phenyloctanediamide).

* * * * *